(12) United States Patent
Rogers et al.

(10) Patent No.: US 11,826,527 B2
(45) Date of Patent: Nov. 28, 2023

(54) NEEDLE ASSEMBLY WITH NEEDLE SAFETY SHIELD

(71) Applicant: KURIN, INC., San Diego, CA (US)

(72) Inventors: Bobby E. Rogers, San Diego, CA (US); David Karl Stroup, San Diego, CA (US)

(73) Assignee: KURIN, INC., San Diego, CA (US)

( * ) Notice: Subject to any disclaimer, the term of this patent is extended or adjusted under 35 U.S.C. 154(b) by 0 days.

(21) Appl. No.: 16/045,321

(22) Filed: Jul. 25, 2018

(65) Prior Publication Data

US 2019/0030293 A1      Jan. 31, 2019

Related U.S. Application Data

(60) Provisional application No. 62/612,184, filed on Dec. 29, 2017, provisional application No. 62/536,929, filed on Jul. 25, 2017.

(51) Int. Cl.
*A61M 25/06* (2006.01)
*A61M 5/32* (2006.01)
(Continued)

(52) U.S. Cl.
CPC ........ *A61M 25/0637* (2013.01); *A61M 5/158* (2013.01); *A61M 5/3257* (2013.01);
(Continued)

(58) Field of Classification Search
CPC .. A61M 5/158; A61M 5/1626; A61M 5/3234; A61M 5/3257; A61M 5/326;
(Continued)

(56) References Cited

U.S. PATENT DOCUMENTS

| 3,859,998 A | 1/1975 | Thomas |
| 3,886,930 A | 6/1975 | Ryan |

(Continued)

FOREIGN PATENT DOCUMENTS

| CN | 1404884 | 3/2003 |
| CN | 1842353 | 10/2006 |

(Continued)

OTHER PUBLICATIONS

European Patent Office; International Search Report and Written Opinion PCT/US2018/043731; dated Oct. 30, 2018; 12 pages.

(Continued)

*Primary Examiner* — Emily L Schmidt
*Assistant Examiner* — Alexandra Lalonde
(74) *Attorney, Agent, or Firm* — Pillsbury Winthrop Shaw Pittman LLP

(57) ABSTRACT

A safety needle assembly includes a housing and a cannula hub connected within a side wall of the housing, a needle connected to the cannula and extending from the cannula hub outward from a proximal end of the housing, and a spring connected with the housing. The assembly includes a barrel connected with the spring and at least partially contained within the housing to least partially cover the cannula hub. The barrel is configured for moving, sliding, traveling, activating, relocating, or transitioning from a first mode in which the barrel is securely retracted and locked at least partially within the housing and the needle extends through an aperture of the barrel and the proximal end of the housing, to a second mode in which the barrel extends from the proximal end and beyond the needle.

9 Claims, 22 Drawing Sheets

(51) Int. Cl.
*A61M 5/158* (2006.01)
*A61M 5/162* (2006.01)

(52) U.S. Cl.
CPC ......... *A61M 5/1626* (2013.01); *A61M 5/3271* (2013.01); *A61M 25/0618* (2013.01); *A61M 2005/325* (2013.01); *A61M 2005/3247* (2013.01); *A61M 2005/3249* (2013.01)

(58) Field of Classification Search
CPC .............. A61M 5/3271; A61M 5/3216; A61M 2005/3252; A61M 2005/3261; A61M 2005/3263; A61M 2005/3249; A61M 2005/325; A61M 25/0637; A61M 25/0618; A61M 25/0631; A61M 2005/3247; A61M 2005/3254; A61M 5/162; A61M 5/321; A61M 2005/1585; A61M 2005/206; A61M 25/06; A61M 25/0612; A61M 25/0625; A61B 5/15003; A61B 5/150389; A61B 5/150656; A61B 5/15074

See application file for complete search history.

(56) References Cited

U.S. PATENT DOCUMENTS

| | | | |
|---|---|---|---|
| 4,207,870 A | 6/1980 | Eldridge | |
| 4,373,535 A | 2/1983 | Martell | |
| 4,690,154 A | 9/1987 | Woodford | |
| 5,097,842 A | 3/1992 | Bonn | |
| 5,658,259 A * | 8/1997 | Pearson | A61M 5/2033 604/232 |
| 5,865,803 A | 2/1999 | Major | |
| 5,873,841 A | 2/1999 | Brannon | |
| 6,013,037 A | 1/2000 | Brannon | |
| 6,540,732 B1 * | 4/2003 | Botich | A61B 10/02 604/413 |
| 6,913,580 B2 | 7/2005 | Stone | |
| 8,439,870 B2 | 5/2013 | Moyer et al. | |
| 8,535,241 B2 | 9/2013 | Bullington | |
| 11,213,232 B2 | 1/2022 | Ivosevic | |
| 2002/0103464 A1 * | 8/2002 | Crawford | A61B 5/150389 604/263 |
| 2005/0119627 A1 * | 6/2005 | Crawford | A61M 5/3243 604/263 |
| 2005/0273019 A1 | 12/2005 | Conway | |
| 2006/0189936 A1 * | 8/2006 | Carlyon | A61M 25/0637 604/110 |
| 2007/0066937 A1 | 3/2007 | Jones et al. | |
| 2007/0185456 A1 * | 8/2007 | Nakajima | A61M 5/3257 604/164.08 |
| 2008/0114296 A1 * | 5/2008 | Saulenas | A61M 25/0631 604/110 |
| 2009/0149812 A1 * | 6/2009 | MacAulay | A61M 5/427 604/117 |
| 2009/0234322 A1 * | 9/2009 | Fischer | A61M 5/346 604/512 |
| 2010/0286611 A1 * | 11/2010 | Schraga | A61M 5/3257 604/110 |
| 2011/0071469 A1 * | 3/2011 | Wilson | A61M 25/0631 604/110 |
| 2011/0152755 A1 * | 6/2011 | Schmalz | A61D 7/00 604/60 |
| 2013/0189643 A1 * | 7/2013 | Infanger | A61M 5/3243 433/90 |
| 2015/0005666 A1 | 1/2015 | Terasawa et al. | |
| 2015/0351678 A1 | 12/2015 | Bullington | |
| 2017/0181734 A1 | 6/2017 | Tzachar | |
| 2022/0160271 A1 | 5/2022 | Ivosevic | |

FOREIGN PATENT DOCUMENTS

| | | |
|---|---|---|
| CN | 106890384 A | 6/2017 |
| EP | 1221301 A2 | 7/2002 |
| EP | 1790374 A1 | 5/2007 |
| EP | 1985324 A1 | 10/2008 |
| JP | 2007143876 | 6/2007 |
| JP | 2008504934 | 2/2008 |
| WO | 2015118109 A1 | 8/2015 |

OTHER PUBLICATIONS

China National Intellectual Property Administration; First Office Action for CN 201880050411.8, dated Jun. 30, 2021, 14 pages.
*Retractable Techs., Inc.* v. *Becton Dickinson & Co.,* CA No. 2:07-CV-250, Claim Construction Order (E.D. Tex., Jan. 20, 2009). 20 pages.
Hillyer, Christopher D., et al. "Bacterial Contamination of Blodd Components: Risks, Strategies and Regulation," Hematology, 2003, pp. 575-589.
De Korte, Dirk, et al. "Diversion of first blood volume results in a reduction of bacterial contamination for whole-blood collections." Vox sanguinis 83.1 (2002): 13-16.
Brecher, Mark E., et al. "Bacterial contamination of blood components." Clinical microbiology reviews 18.1 (2005): 195-204.
Van Zundert, Adrien. "New closed IV catheter system." Acta Anæsthesiologica Belgica 56.3 (2005): 283-285.
Hall, Keri K., et al. "Updated review of blood culture contamination." Clinical microbiology reviews 19.4 (2006): 788-802.
Li, Yiwen, et al. "Direct labeling and visualization of blood vessels with lipophilic carbocyanine dye DiI." Nature protocols 3.11 (2008): 1703-1708.
Page, Catherine, et al. "Blood conservation devices in critical care: a narrative review." Annals of intensive care 3 (2013): 1-6.
Abbott Point of Care, Cartridge and Test Information, Art: 714258-01O; Rev. Date: Aug. 15, 2016, 1-6 pages.
Zimmon, David S. et al. "Effect of portal venous blood flow diversion on portal pressure." The Journal of Clinical Investigation 65.6 (1980): 1388-1397.
Patton, Richard G., et al. "Innovation for reducing blood culture contamination: initial specimen diversion technique." Journal of clinical microbiology 48.12 (2010): 4501-4503.
Tang, Menglin, et al. "Closed blood conservation device for reducing catheter-related infections in children after cardiac surgery." Critical Care Nurse 34.5 (2014): 53-60.
Ernst, Dennis J. et al. "NCCLS simplifies the order of draw: a brief history." MLO: medical laboratory observer 36.5 (2004): 1-5 pages.
Gottlieb, T. "Hazards of bacterial contamination of blood products." Anaesthesia and intensive care 21.1 (1993): 20-23.
Norberg, Alonna, et al. "Contamination rates of blood cultures obtained by dedicated phlebotomy vs intravenous catheter." Jama 289.6 (2003): 726-729.
Quilici, Nathalie, et al. "Differential quantitative blood cultures in the diagnosis of catheter-related sepsis in intensive care units." Clinical infectious diseases 25.5 (1997): 1066-1070.
Napolitano, Marcello, et al. "Quality control of bacterial contamination of blood components: the feasibility of diversion system testing." Blood Transfus 2 (2004): 231-232.
De Korte, Dirk, et al. "Effects of skin disinfection method, deviation bag, and bacterial screening on clinical safety of platelet transfusions in the Netherlands." Transfusion 46.3 (2006): 476-485.
Liumbruno, Giancarlo Maria, et al. "Reduction of the risk of bacterial contamination of blood components through diversion of the first part of the donation of blood and blood components." Blood Transfusion 7.2 (2009): 86.
NCCLS. Procedures for the Collection of Diagnostic Blood Specimens by Venipuncture; Approved Standard—Fifth Edition. H3-A5, vol. 23, No. 32. Replaces H3-A4; vol. 18, No. 7. 1-52 pages. http://demo.nextlab.ir/Organization/Documents/CLSI-Standards/CLSI-H3-A5.aspx.
Challiner, A., et al. "Venous/arterial blood management protection system." Anaesthesia 47.2 (1992): 169-169.
Murphy, Michael F. "Better Blood Transfusion." Journal of the Intensive Care Society 4.3 (2003): 78-80.
Palavecino, Elizabeth L., et al. "Detecting bacterial contamination in platelet products." Clinical laboratory 52.9-10 (2006): 443-456.

(56) References Cited

OTHER PUBLICATIONS

Sheppard, Chelsea A., et al. "Bacterial contamination of platelets for transfusion: recent advances and issues." Laboratory Medicine 36.12 (2005): 767-770.

Shulman, Gerald. "Quality of processed blood for autotransfusion." Journal of Extracorporeal Technology 32.1 (2000): 11-19.

Weinbaum, Fredric I., et al. "Doing it right the first time: quality improvement and the contaminant blood culture." Journal of Clinical Microbiology 35.3 (1997): 563-565.

Weinstein, Melvin P. "Blood culture contamination: persisting problems and partial progress." Journal of clinical microbiology 41.6 (2003): 2275-2278.

Weinstein, Melvin P., et al. "The clinical significance of positive blood cultures in the 1990s: a prospective comprehensive evaluation of the microbiology, epidemiology, and outcome of bacteremia and fungemia in adults." Clinical Infectious Diseases 24.4 (1997): 584-602.

Weinstein, Melvin P. "Current blood culture methods and systems: clinical concepts, technology, and interpretation of results." Clinical infectious diseases 23.1 (1996): 40-46.

Closed IV, BD Saf-T-Intima. "Catheter System, Becton, Dickinson and Company, Brochure." Retrieved from the Internet (Aug. 23, 2019). 4 pages.

Perez, P., et al. "Multivariate analysis of determinants of bacterial contamination of whole-blood donations." Vox Sanguinis 82.2 (2002): 55-60.

McDonald, Carl P. "Interventions implemented to reduce the risk of transmission of bacteria by transfusion in the English National Blood Service." Transfusion Medicine and Hemotherapy 38.4 (2011): 255-258.

Lifesciences, Edwards. "Conservation. Safety. Simplicity. Edwards VAMP and VAMP Jr. Systems." (2002). 4 pages.

Sheppard, et al., Bacterial Contamination of Platelets for Transfusion: Recent Advances and Issues, Labmedicine, vol. 36, No. 12, Dec. 2005 ("Sheppard 2005").

\* cited by examiner

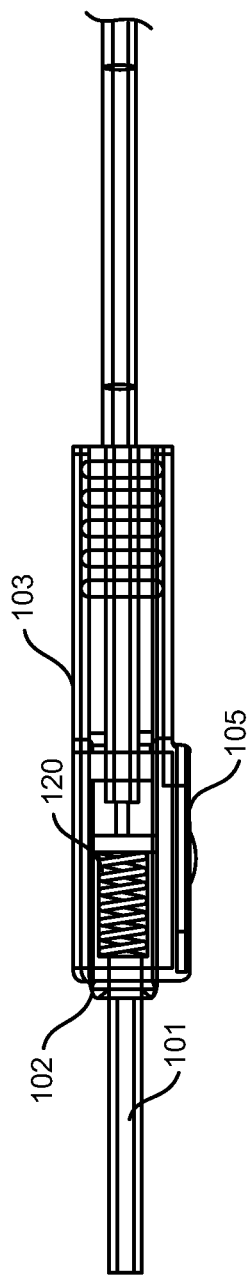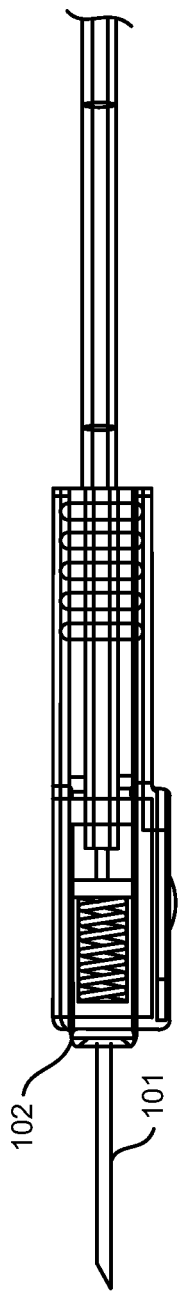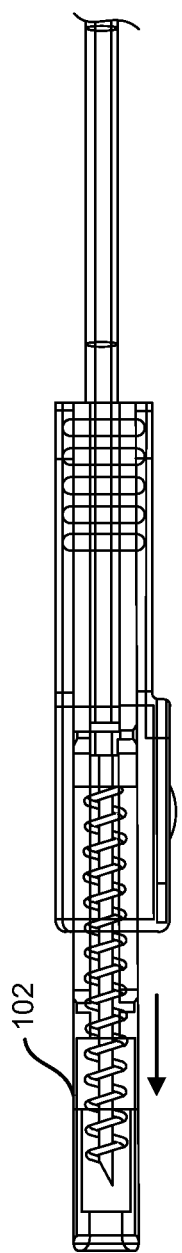

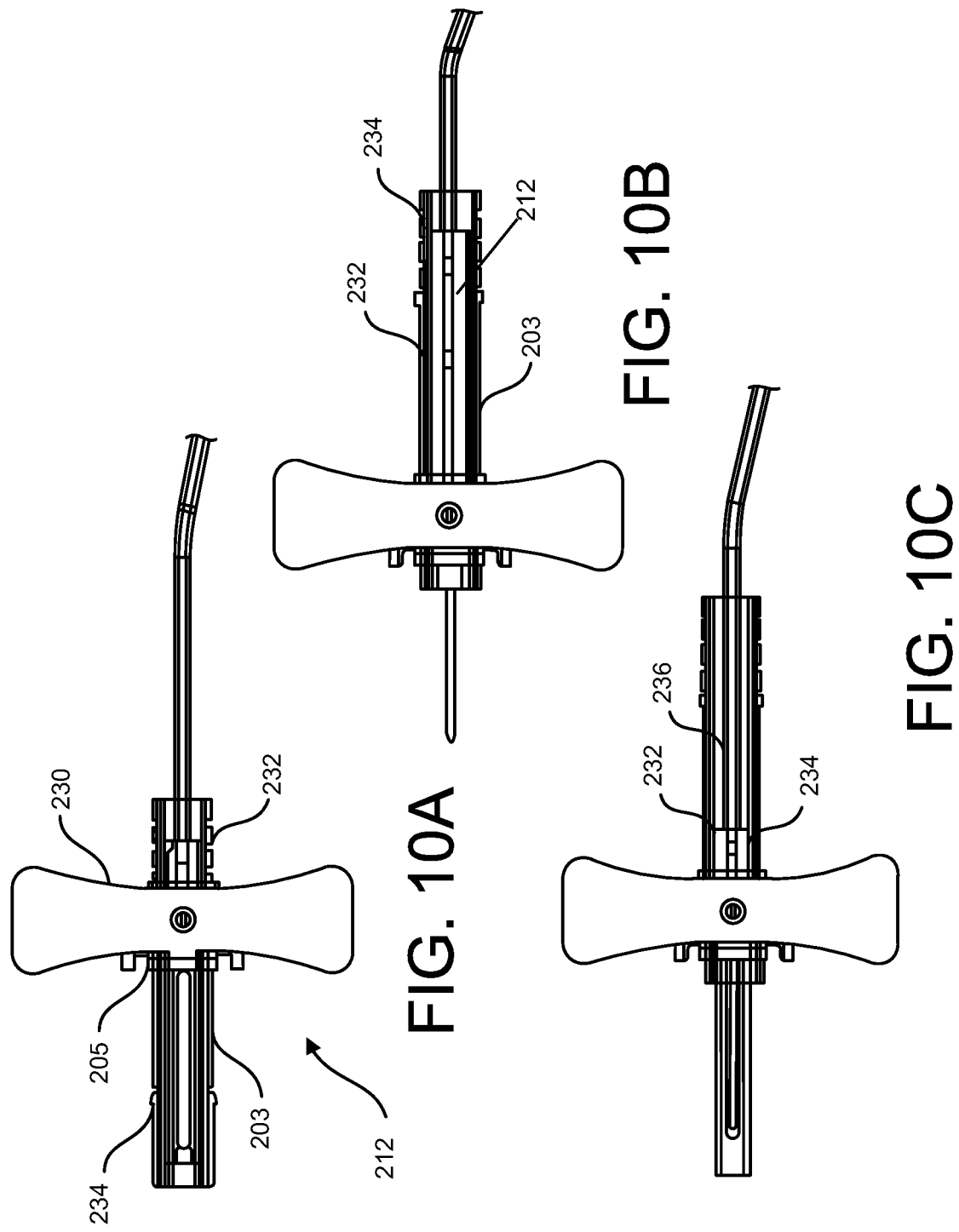

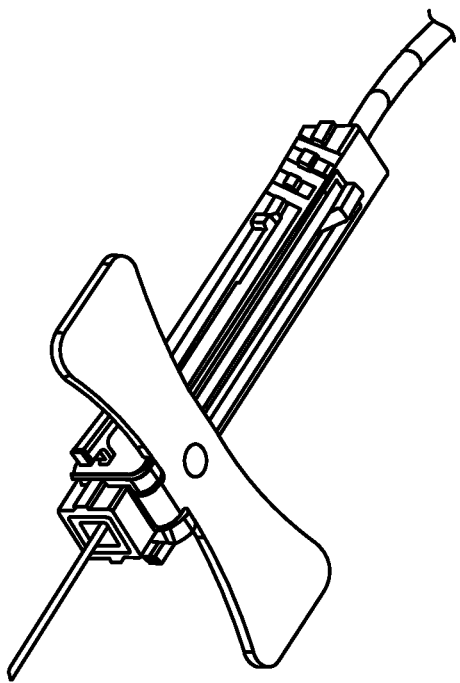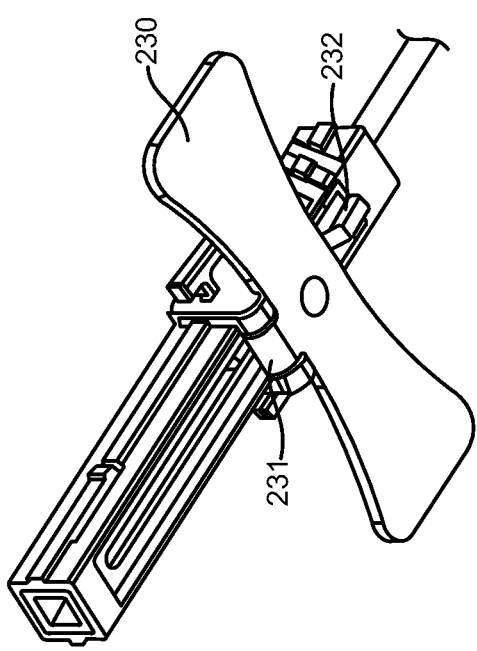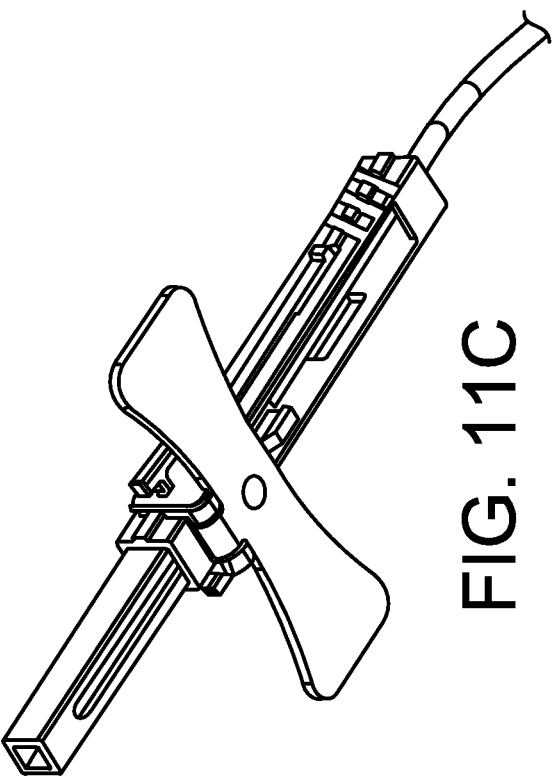
FIG. 11A
FIG. 11B
FIG. 11C

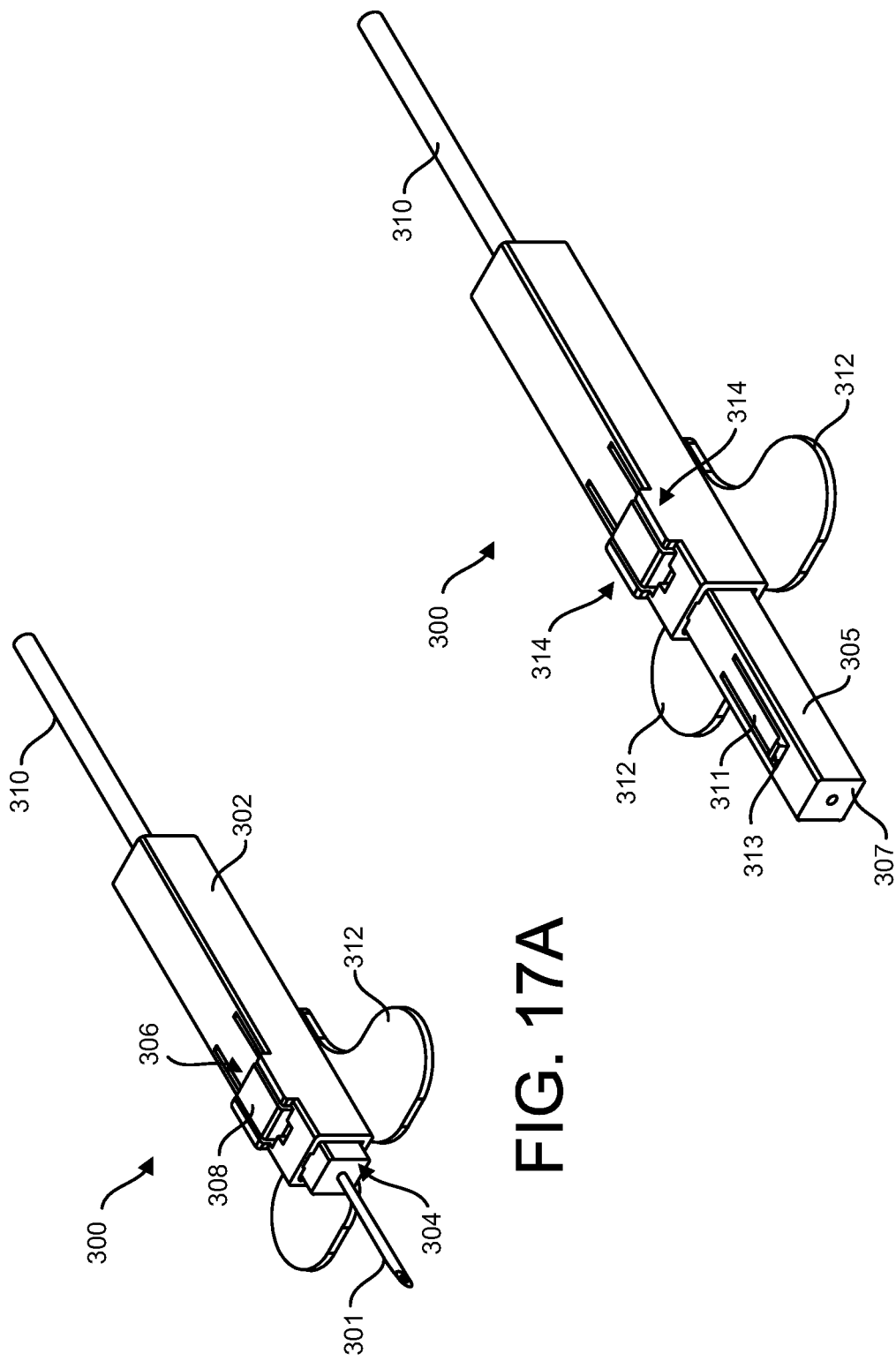

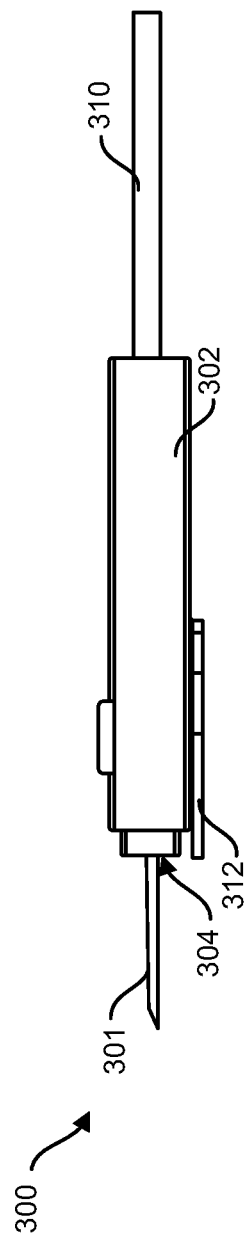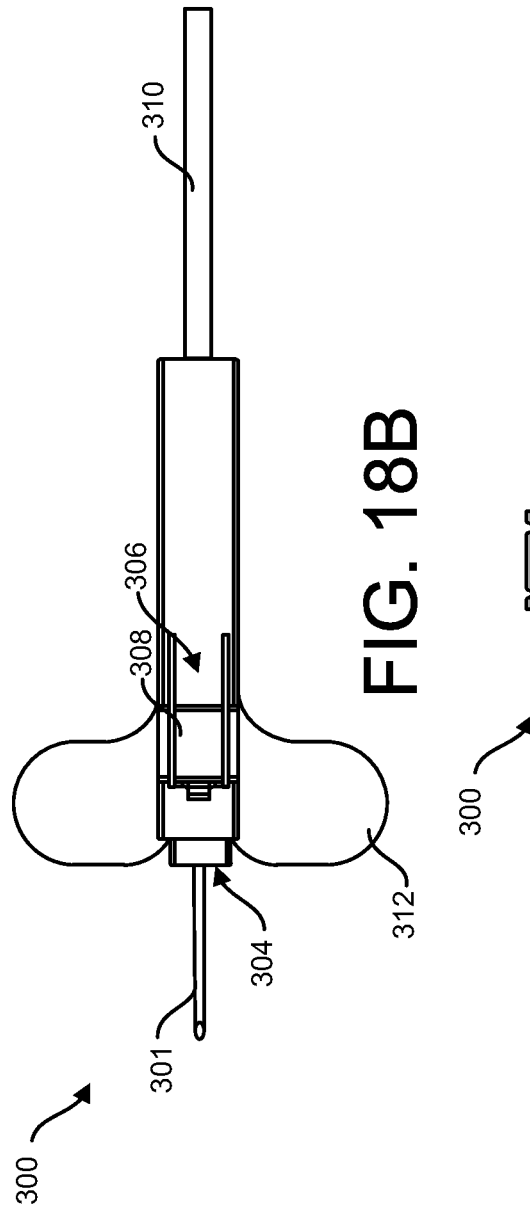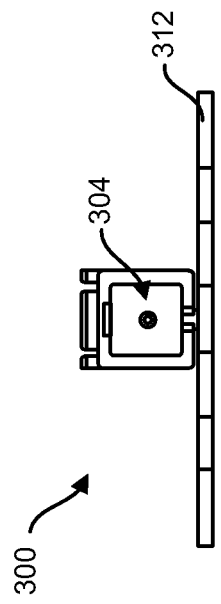

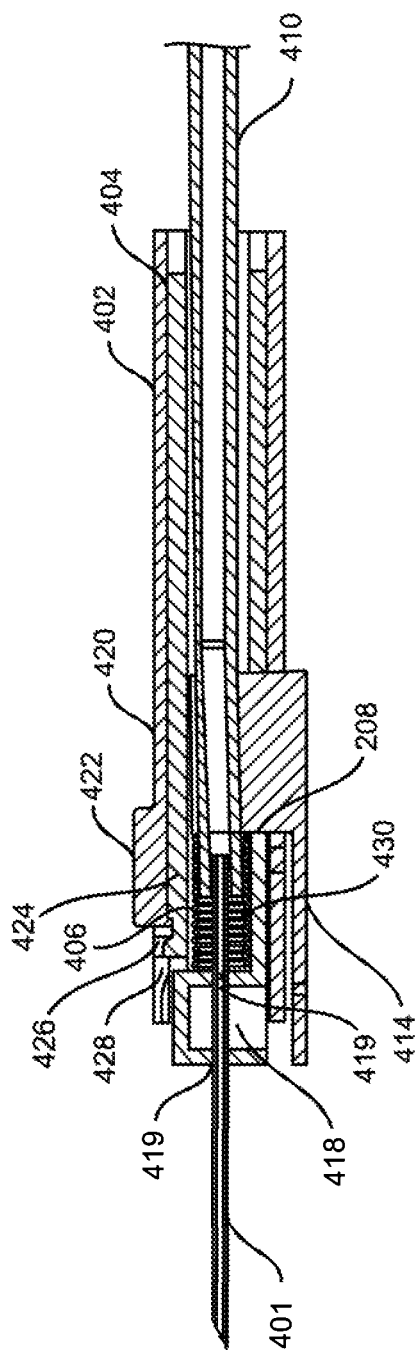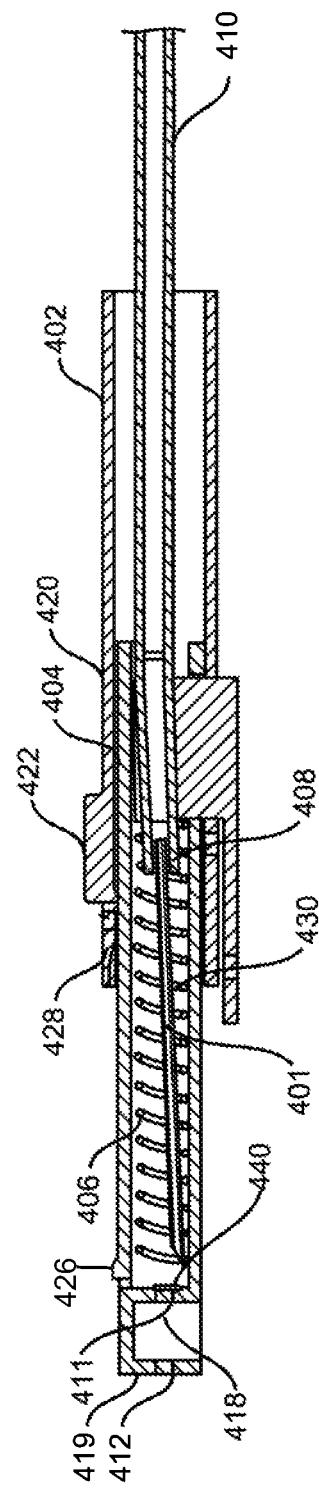

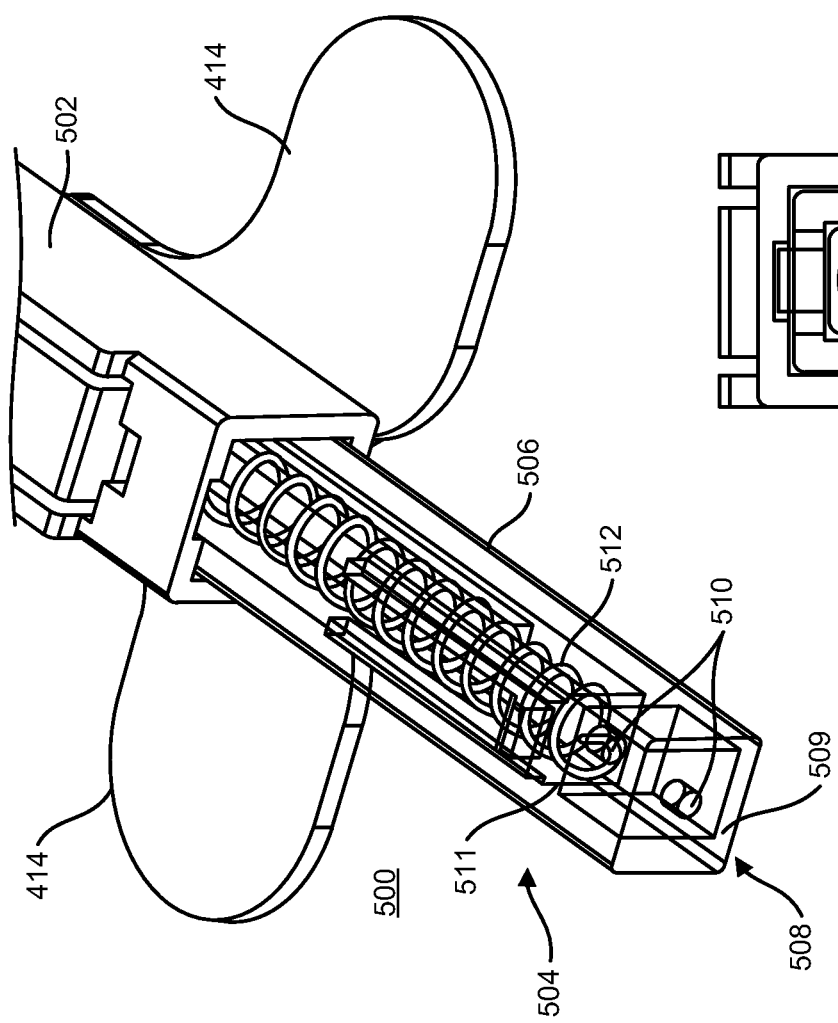
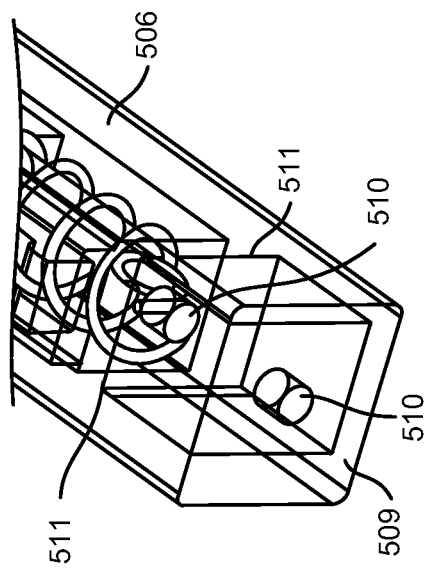
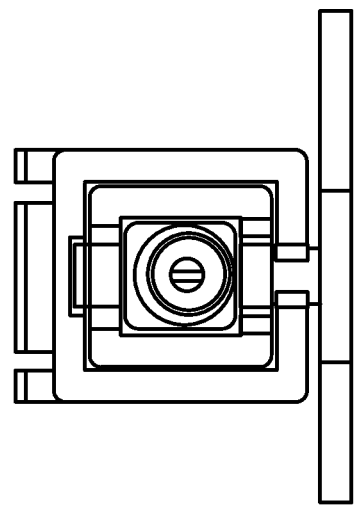
FIG. 21A
FIG. 21B
FIG. 21C

NEEDLE ASSEMBLY WITH NEEDLE SAFETY SHIELD

CROSS-REFERENCE TO RELATED APPLICATIONS

This application claims the benefit of U.S. Provisional Application No. 62/536,929, filed Jul. 25, 2017, and also claims the benefit of U.S. Provisional Application No. 62/612,184, filed Dec. 29, 2017. Each of these applications is incorporated herein by reference in its entirety.

BACKGROUND

Intravenous access by a needle is performed in a medical setting for collecting bodily fluids from a patient and infusing liquids into a patient. These procedures are usually performed using what is known as fluid collection sets and intravenous infusion sets. Such sets typically include flexible plastic tubing with a proximal end connected to a port and a distal end connected to a needle assembly.

Conventional needle assemblies include a hub and a needle cannula. Most needle assemblies further include a pair of flexible wings extending out from the hub or from near the hub, which can be folded toward each other to form a convenient handle for gripping by a technician to guide and manipulate the needle cannula. The wings can also be extended outward and laid flat for being taped to a skin surface area of a patient to secure the needle cannula in a desired position, i.e. after venipuncture.

One problem with the use of needle assemblies is inadvertent or accidental skin punctures with the needle, called "sticks," particularly after venipuncture and use. Accidental sticks can be painful, and may even transmit disease or pathogens from the patient to another person. Some conventional needle assemblies therefore employ a retractable needle, i.e. a system for permanently retracting the needle into a housing the forms at least part of the hub. Once retracted by a force, such as from a spring, the needle is permanently locked inside the housing.

However, several problems exist with a retractable needle assembly. One problem is premature or inadvertent retraction, where technician accidently presses an actuator such as a button to retract the needle before desired. This problem can occur even when the needle is inserted into a patient's vein, in which such retraction can be painful and often damaging the vein or surrounding tissue.

Another problem is with an actuator of such retraction assembly. Depending on where the actuator is located on the needle assembly, such actuation may require both hands of the technician, which is undesirable. On the other hand, if the actuator is conveniently located so as to require only one hand of the technician, then premature or inadvertent retraction is much more likely.

SUMMARY

This document describes a needle assembly for intravenous access, the needle assembly including a needle safety shield that can be deployed after intravenous access, to cover the needle to avoid inadvertent needle sticks. The needle safety shield is part of a safety mechanism that includes an actuator that is optimally located on the needle assembly to allow one-handed operation of the needle assembly and deployment of the needle safety shield, while being configured to limit or avoid inadvertent activation of the actuator and deployment of the needle safety shield.

In some implementations, a safety needle assembly includes a housing, and a cannula extending from the housing, the cannula including a needle for venipuncture of a patient. The safety needle assembly further includes a pair of wings extending from opposing sides of the housing, and a trigger integrated with the housing. The safety needle assembly further includes a safety shield that is at least partially covered in the housing in a first mode, and which at least partially covers the needle in a second mode. The safety shield further includes a locking mechanism and a biasing mechanism, the locking mechanism locking the safety shield in the first mode, and the biasing mechanism moving the safety shield between the first mode to the second mode under actuation by the trigger.

In alternative implementations, a safety needle assembly includes a housing, and a safety shield adapted to be secured in a first mode to be substantially locked within the housing in a first mode, and extended from the housing in a second mode. The safety needle assembly further includes a cradle that includes a cannula bond well connected with a cannula that includes a needle for venipuncture of a patient, the cradle being movable from a first position in which the needle is retracted in the housing, to a second position in which the needle is extended from the housing and the cradle is locked in the second position. The safety needle assembly further includes an elastomeric band coupled between the safety shield and the cradle, the elastomeric band being charged by moving the cradle from the first position to the second position, and which propels the safety shield to the second mode to at least partially cover the needle by actuating a release mechanism of the safety shield from the first mode.

In another implementation, the device includes a housing having an outer surface that includes a depressable actuator, a bottom surface of the depressable actuator including a latch. The device further includes a cannula hub mounted in the housing, and including a needle that extends out of the housing. The device further includes a barrel that is retractable into the housing against a compressed spring in a first mode to expose the needle through a front hole in the barrel, the barrel having a locking member that interacts with the latch of the actuator to lock the barrel in the first mode, the barrel having a second mode in which the actuator is depressed to disengage the locking member from the latch to remove resistance to the spring, which causes the barrel to extend out from the housing to cover all of the needle that extends out of the housing.

In some aspects, a safety needle assembly for venipuncture of a patient is described. The safety needle assembly includes a housing having a proximal end, a distal end, and a side wall therebetween. The safety needle assembly further includes a cannula connected with the housing and configured for conveying a fluid. The safety needle assembly further includes a needle connected to the cannula and extending from the cannula outward from the proximal end of the housing, and a spring having a first end and a second end, the second end being connected with an interior wall of the housing. The safety needle assembly further includes a barrel connected with the first end of the spring and at least partially contained within the housing to least partially cover the cannula hub, the barrel having an outer face at the proximal end of the housing, the outer face including an aperture, the barrel further being configured for transitioning from a first mode in which the barrel is securely retracted and locked at least partially within the housing and the needle extends through the aperture of the outer face of the barrel and the proximal end of the housing sufficient for the venipuncture of the patient, to a second mode in which the barrel extends from the proximal end of the housing and beyond the needle such that the needle is contained within the barrel on an opposite side of the outer face.

In other aspects, a safety needle assembly includes a cannula for conveying a fluid, and a needle connected to the cannula for the venipuncture of the patient for withdrawing and/or delivering the fluid. The safety needle assembly further includes a housing having a proximal end, a distal end, and a side wall therebetween, the housing further including a cannula hub connected within the side wall of the housing to hold the cannula and/or needle such that the needle extends outward from the proximal end of the housing, the housing further containing a spring having a first end and a second end, the second end of the spring being connected with an interior wall of the housing. The safety needle assembly further includes a barrel connected with the first end of the spring and at least partially contained within the housing to least partially cover the cannula hub, the barrel having an outer face at the proximal end of the housing, the outer face including an aperture, the barrel further being configured for transitioning from a first mode in which the barrel is securely retracted and locked at least partially within the housing and the needle extends through the aperture of the outer face of the barrel and the proximal end of the housing sufficient for the venipuncture of the patient, to a second mode in which the barrel extends from the proximal end of the housing and beyond the needle such that the needle is contained within the barrel on an opposite side of the outer face.

In yet other aspects a safety needle assembly for connecting with a cannula adapted for conveying a fluid to or from a patient is described. The safety needle assembly includes a housing having a proximal end, a distal end, and a side wall therebetween, the housing further including a cannula hub connected within the side wall of the housing. The safety needle assembly further includes a needle connected to the cannula and extending from the cannula hub outward from the proximal end of the housing, and a spring having a first end and a second end, the second end being connected with an interior wall of the housing. The safety needle assembly further includes a barrel connected with the first end of the spring and at least partially contained within the housing to least partially cover the cannula hub, the barrel having an outer face at the proximal end of the housing, the outer face including an aperture, the barrel further being configured for moving, sliding, traveling, activating, relocating, or transitioning from a first mode in which the barrel is securely retracted and locked at least partially within the housing and the needle extends through the aperture of the outer face of the barrel and the proximal end of the housing sufficient for the venipuncture of the patient, to a second mode in which the barrel extends from the proximal end of the housing and beyond the needle such that the needle is contained within the barrel on an opposite side of the outer face.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

FIGS. 2A-2C illustrate various states of a needle assembly with a safety shield in each of a number of modes;

FIGS. 10A-10C show a bottom view of the needle assembly 200 shown in FIGS. 8A-8C and 9A-9C;

FIGS. 11A-11C show a perspective view of the needle assembly 200 shown in FIGS. 8A-8C and 9A-9C;

FIGS. 17A and 17B illustrate a needle assembly in accordance with implementations described herein;

FIGS. 18A-18C are various views of the needle assembly in the first mode in accordance with the implementations described herein;

FIGS. 20A and 20B are cross-sectional, cutaway views of the needle assembly in the first mode and second mode, respectively;

FIGS. 21A-21C illustrate a needle assembly, and in particular a barrel of a needle assembly.

Like reference symbols in the various drawings indicate like elements.

DETAILED DESCRIPTION

This document describes a needle assembly for intravenous access, the needle assembly including a needle safety shield that can be deployed after intravenous access, to cover the needle to avoid inadvertent needle sticks. The needle safety shield is part of a safety mechanism that includes an actuator that is optimally located on the needle assembly to allow one-handed operation of the needle assembly and deployment of the needle safety shield, while being configured to limit or avoid inadvertent activation of the actuator and deployment of the needle safety shield.

Figure 1B:
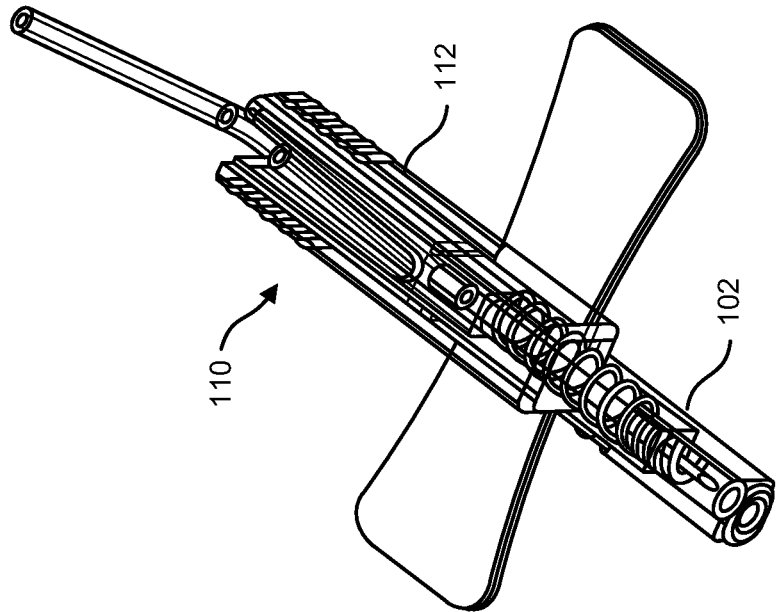
FIGS. 1A and 1B illustrate a needle assembly having needle and a deployable needle safety shield.
Figure 1A:
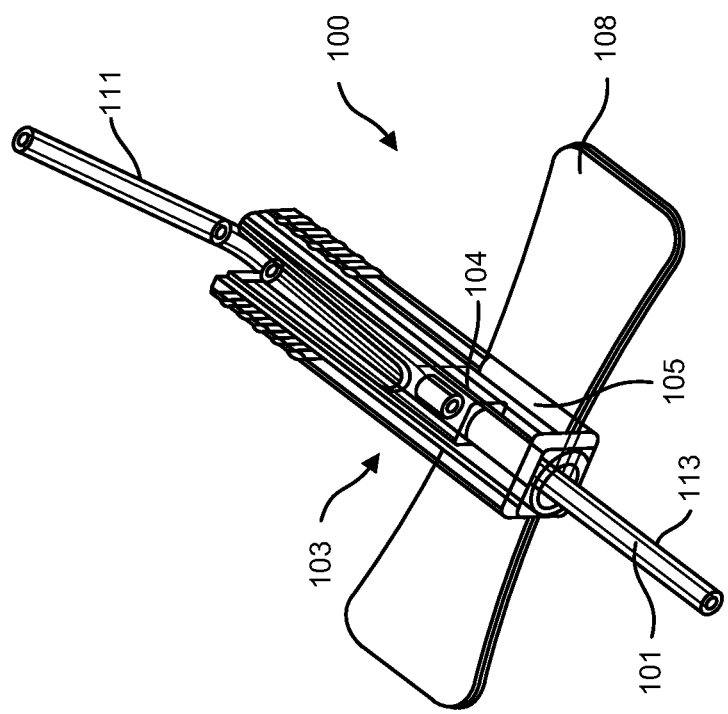

FIGS. 1A and 1B illustrate a needle assembly 100 having needle 101 and a deployable needle safety shield 102. The needle assembly 100 includes a cannula hub 104 formed of a housing 103 from which a needle 101 extends. As shipped, the needle 101 is preferably covered by a removable shield 113 such as a plastic tube or the like. The housing 103 houses or at least partially surrounds the safety shield 102, which in turn at least partially surrounds the cannula hub 104 and which is initially retracted into the housing 103 and can be deployed to extend out of the housing 103 to cover the needle 101 post-use. The cannula hub 104 can be connected with tubing 111 or other fluid pathway or conveyance mechanism at an end opposite the needle 101.

The housing 103 includes a main housing portion 105 from which one or more wings 108 can extend. A technician can either fold up and grasp the wings 108 as a juxtaposed pair to control placement and insertion of the needle 101, or grasp the main housing portion 105 to control such placement and insertion, or even removal, of the needle from a patient. The housing can be made of plastic, such as, but not limited to, polycarbonate, COPE, acrylic, TPE, or the like.

The needle assembly 100 includes a safety mechanism 110 for actuating and deploying the safety shield 102. In some implementations, the safety mechanism includes one or more prongs 112 or extending arms, levers, or the like, and preferably a pair of prongs 112 much like a "clothes pin," extending from the main housing portion 105, and which flex around a fulcrum or mid-point between the pair of prongs 112 and can have three or more prongs 112. Each prong 112 can be straight and angled, and oriented in parallel, or rounded in cross section to form a cylinder.

Each prong 112 is connected at proximal end of the housing 103, and can include a set of ridges or other traction mechanism at a traction region at a distal end. The traction region provides an indication to a technician as to where they should grasp, as well as providing a location for an optimal leverage point for actuating deployment of the safety shield 102. In some implementations, the gripping mechanism extends out from opposing sides of the pair of prongs 112. Post-use of the needle, the safety mechanism 110 can be actuated, such as the technician pressing the distal end of the pair of prongs toward each other, to actuate deployment of the safety shield 102, as will be explained in further detail below.

FIGS. 2A-2C illustrate various states of the needle assembly 100 shown in FIG. 1. FIG. 2A shows the needle assembly 100 with the needle 101 covered or sheathed by a removable cover 113, which extends sufficiently beyond the pointed tip of the needle so as to guard against accidental sticks. In this state, i.e. as shipped, the safety shield 102 is in a retracted mode. In the retracted mode, the safety shield 102 is at least partially or wholly retracted into housing 103, and held in place by a holding mechanism (described below) against a biasing force of a biasing mechanism such as a spring 120 by one or more latches, pins, grooves, detents, ridges, flanges, or the like, between an outer surface of the safety shield 102 and an inner surface of the housing 103, where such holding is sufficient to withstand the biasing force of the biasing mechanism in the retracted mode.

FIG. 2B shows the needle assembly 100 with the cover 113 removed from the needle. While removal of the removable cover 113 is fairly easy, and as shown in FIG. 2B in which the needle assembly 100 is shown as being ready for use, replacing the cover 113 back on the needle is too challenging and risky, and therefore not feasible for providing safety from accidental sticks. Thus, as illustrated in FIG. 2C, the safety shield, which is retracted at least partially or even totally within the housing 103 when the needle assembly 100 is shipped and prior to use, can be actuated and deployed to extend from the housing 103 to cover the needle 101. The safety shield 102 preferably extends a distance beyond the pointed tip of the needle, and is locked in the deployed, extended mode to prevent a person from pushing on a front face of the safety shield. Manipulation or actuation of the prongs 112 will cause a corresponding weakening or removal of the holding force of the holding mechanism such that the biasing force of the biasing mechanism now overcomes the holding force to drive the safety shield 102 outwardly from the housing 103 to provide the safety shield in the deployed mode to at least partially cover the needle 101, and in particular the sharp tip of the needle 101.

Figure 3:
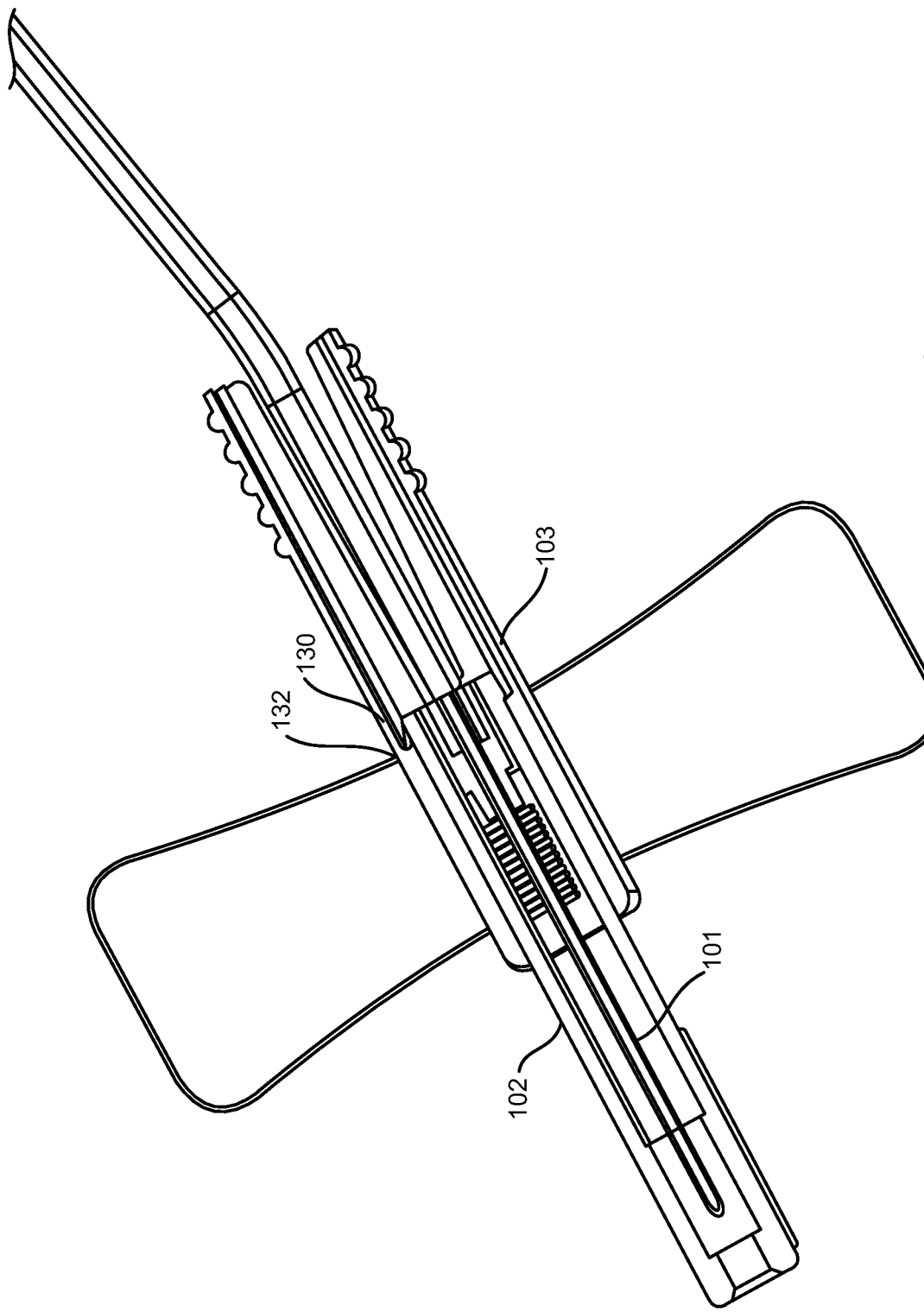
FIG. 3 shows the needle assembly with the safety shield in the deployed mode.

FIG. 3 shows the needle assembly 100 with the safety shield 102 in the deployed mode, where a latch 130 or similar feature on a distal end of the safety shield mates against or with a corresponding latch 132 or similar feature on an inner surface of the housing 103, to stop the safety shield 102 from extending further out of the housing 103 and helping to lock the safety shield 102 in the deployed mode so that it cannot be retracted again into the housing 103.

Figure 4:
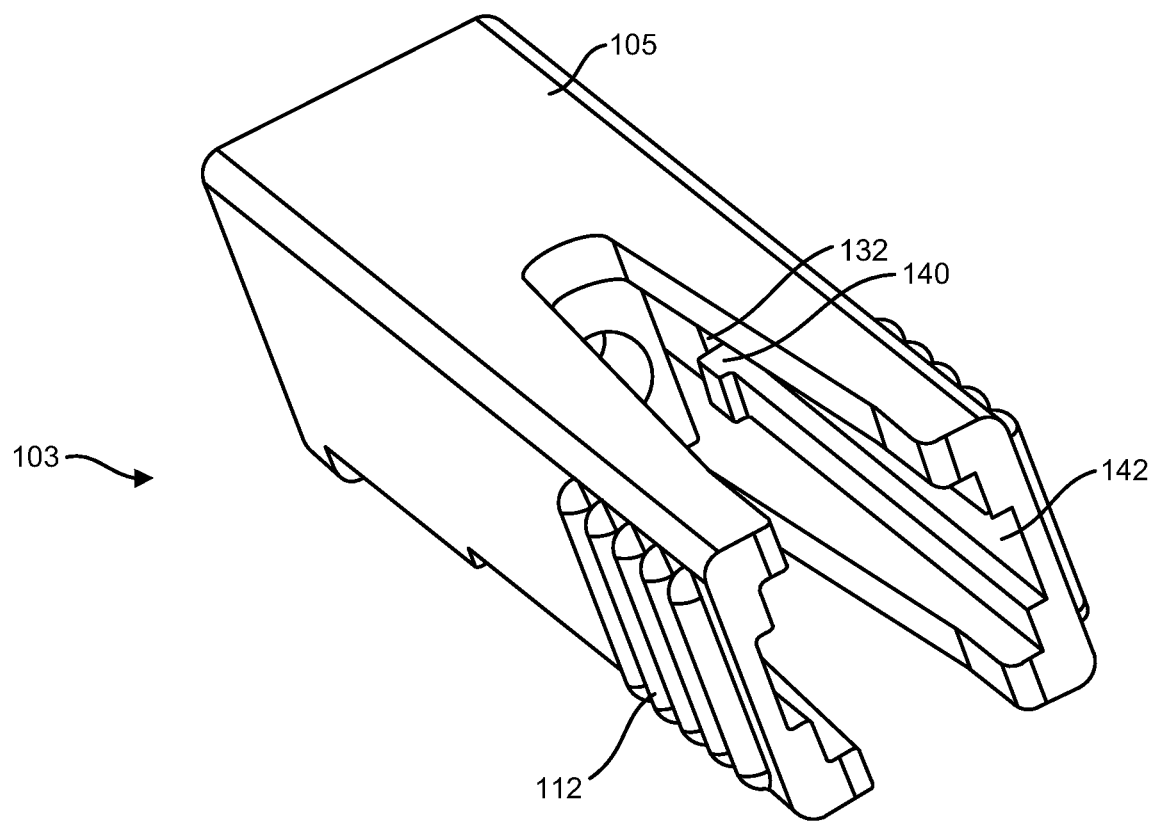
FIG. 4 shows a housing with actuator prongs, and first trigger latches on an inner surface the prongs.

FIG. 4 shows a housing 103 with actuator prongs 112, and first trigger latches 140 on an inner surface of at least one and preferably all prongs 112, positioned toward the junction or fulcrum point between the prongs 112. The first trigger latches 140 are also positioned on either side of a groove or channel 142 in which a corresponding ridge 144 of actuator arms 143 of the safety shield 102 (shown in FIG. 5) can be placed to allow controlled and directed sliding therebetween. In other implementations, the housing 103 can have a ridge and the actuator arms 143 of the safety shield can have the groove. As shown in FIG. 5, the actuator arms 143 include one or more second trigger latches 146 at a proximal end of the actuator arms to latch with the first trigger latches 140 in the retracted mode, i.e. shown in FIG. 2A and FIG. 2B. The one or more second trigger latches 146 of the actuator arms 143 can include one or more second trigger latches 148 at a distal end of the actuator arms 143, as well as a first locking latch 150 (latch 130 in FIG. 3) to mate with corresponding second locking latch (latch 132 in FIG. 3) to lock the safety shield in the deployed mode, as shown in FIG. 2C.

Figure 5A:
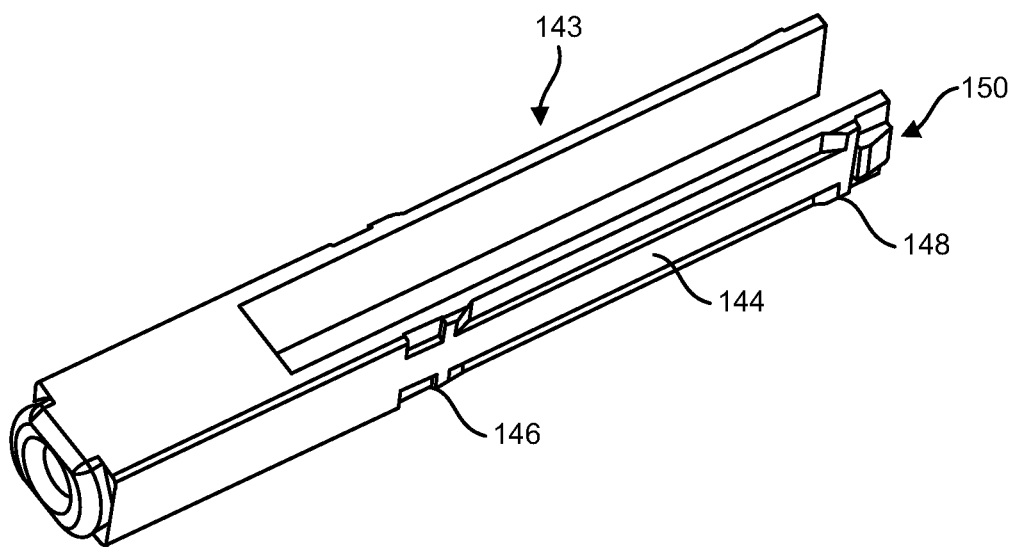
FIGS. 5A, 5B show a safety shield with second and third trigger latches on an outer surface of actuator arms that cooperate with the actuator prongs of the housing.
Figure 5B:
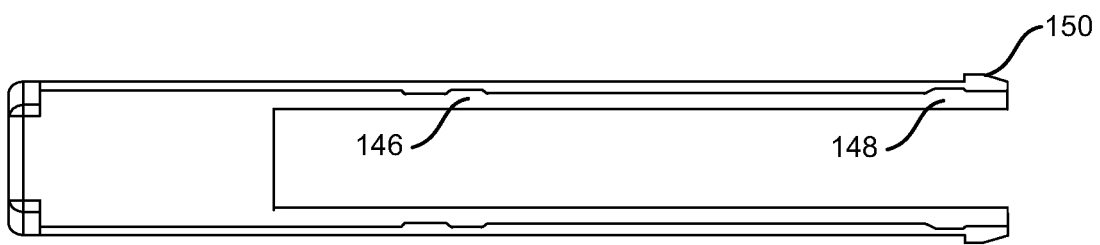

On either side of the second trigger latches 146, 148 can be a slight groove or indentation, to facilitate mating between the first trigger latches 140 and either the second or third trigger latches 146, 148. As can be seen in FIGS. 5A and 5B, pressure at a distal end of the actuator arms 143 of the safety shield, from a technician pressing on the distal end of the prongs 112 at the traction region, causes the second trigger latches 146 to separate from the first trigger latches 140 to allow the biasing force of the biasing mechanism such as the spring to overcome any further latching force, and the safety shield 102 will slide through housing 103 until the locking latches 150 engage their corresponding locking latches on the inner surface of the housing 103.

Figure 6A:
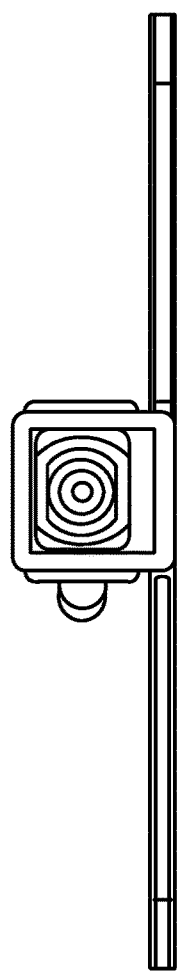
FIGS. 6A, 6B, and 6C show a front view, top-down view, and side view, respectively, of a needle assembly.
Figure 6B:
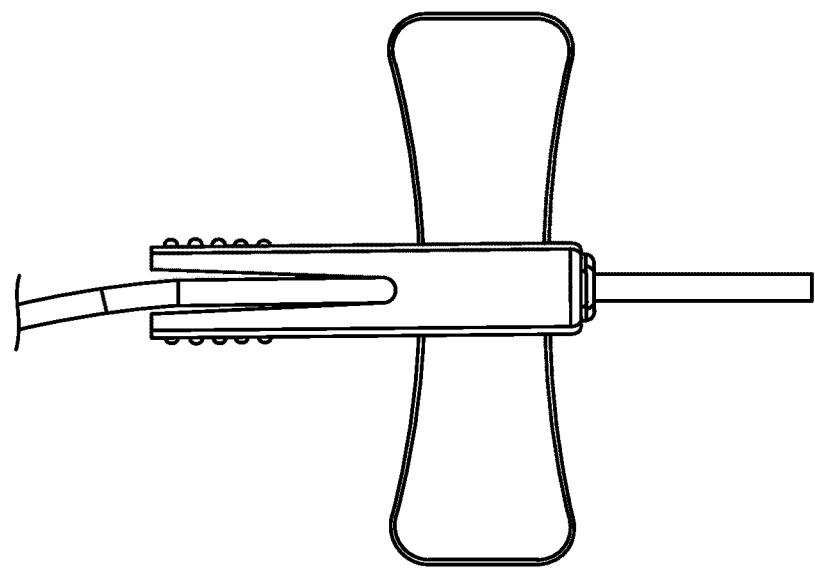
Figure 6C:
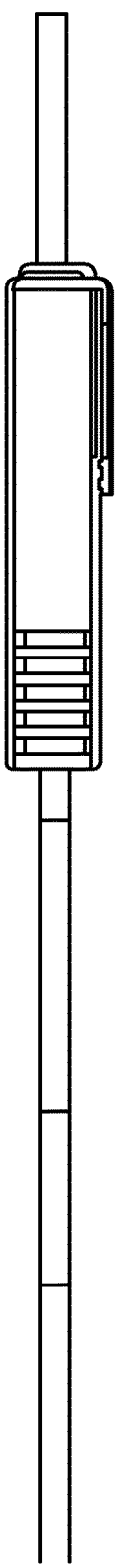
Figure 7A:
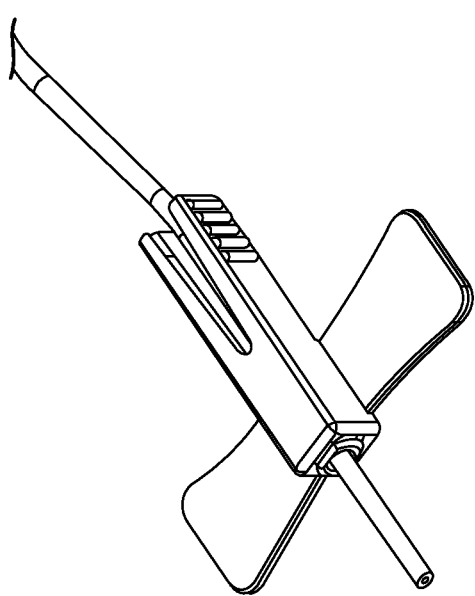
FIGS. 7A, 7B and 7C show a perspective view of a needle assembly in various states or modes, substantially as shown with reference to FIGS. 2A, 2B and 2C.
Figure 7B:
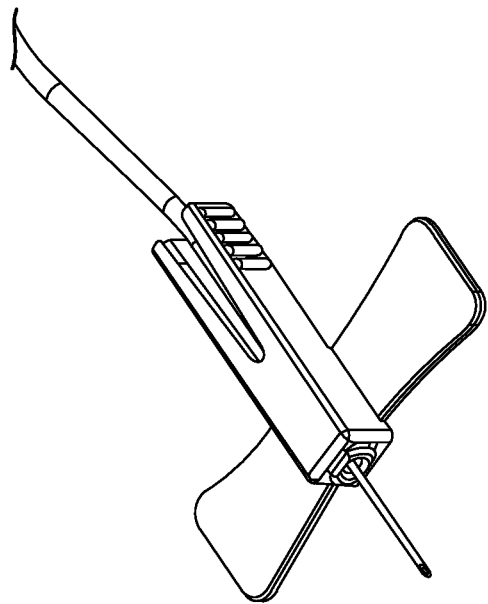
Figure 7C:
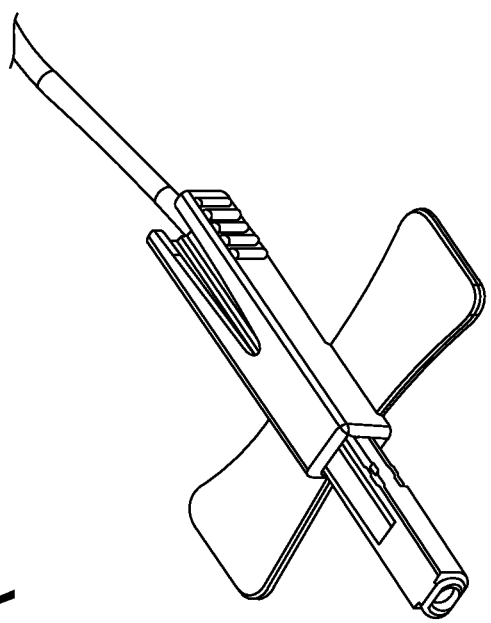

FIGS. 6A, 6B, and 6C show a front view, top-down view, and side view, respectively, of a needle assembly consistent with the disclosure herein. FIGS. 7A, 7B and 7C show a perspective view of a needle assembly in various states or modes, substantially as shown with reference to FIGS. 2A, 2B and 2C.

Figure 8A:
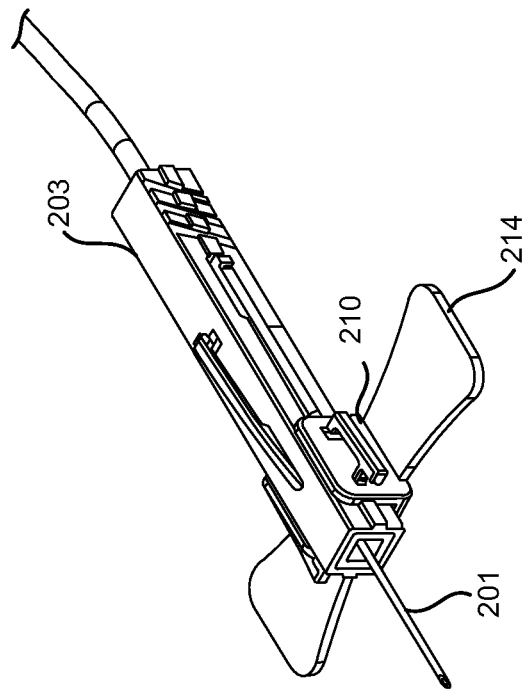
FIGS. 8A-8C illustrate a needle assembly having needle and a deployable needle safety shield, and various states thereof.
Figure 8B:
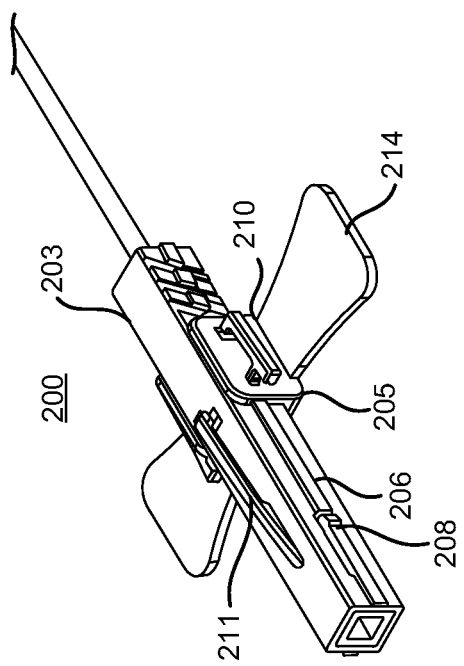
Figure 8C:
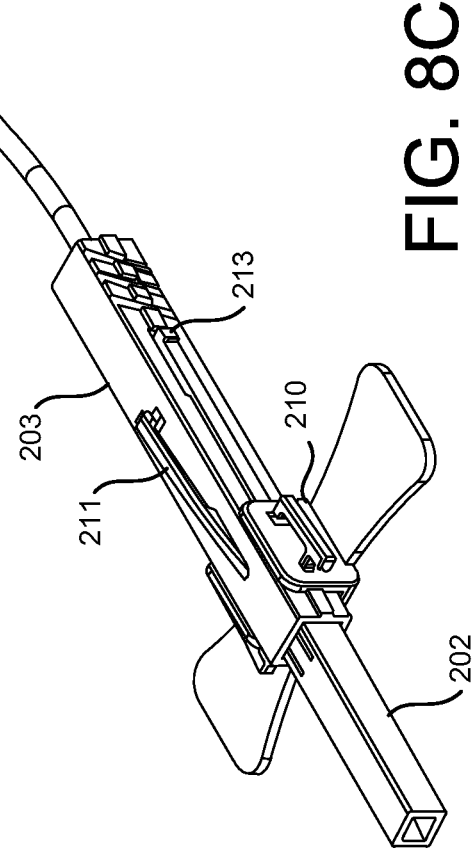
Figure 9A:
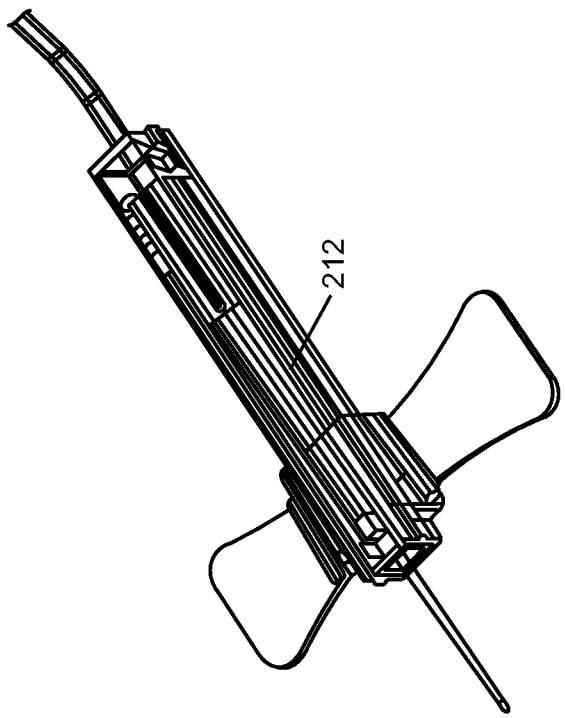
FIGS. 9A-9C are transparent views of the needle assembly and deployable needle safety shield, and various states thereof, as shown in FIGS. 8A-8C.
Figure 9B:
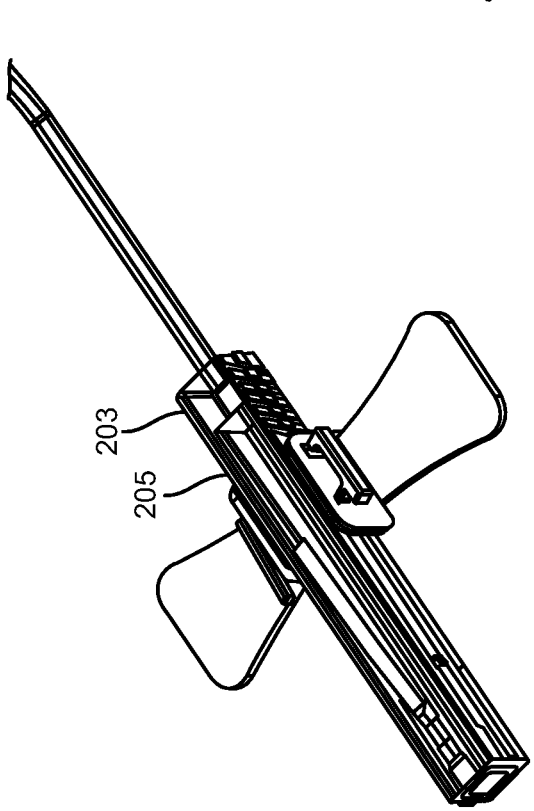
Figure 9C:
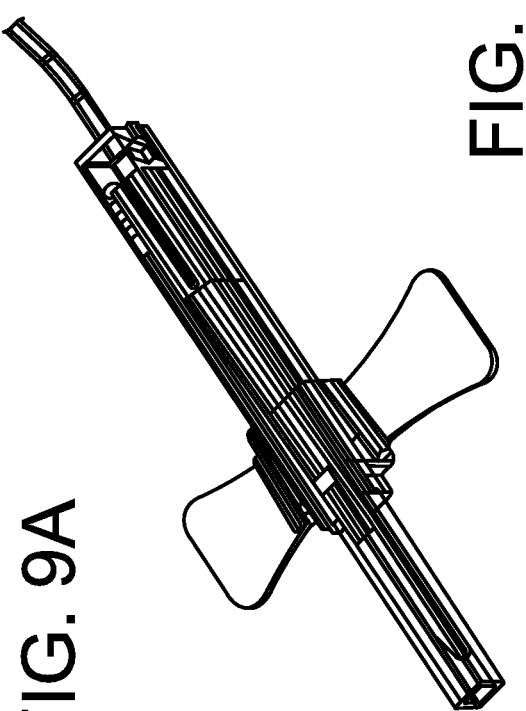

FIGS. 8A-8C illustrate a needle assembly 200 having a needle 201 and a deployable needle safety shield 202 to at least partially cover the needle 201, and protect a tip of the needle 201 against accidental needle sticks. FIGS. 9A-9C are transparent views of the needle assembly and deployable needle safety shield, and various states thereof, as shown in FIGS. 8A-8C. The needle assembly 200 includes a housing 203 and a cradle 205 that slides forward along an outer surface of the housing on a track 206 and is locked in place in a forward position. The cradle 205 is connected through the housing 203 to a cannula hub (not shown) that provides the needle 201. The track 206 can be a groove, a channel, a raised extending member, a combination thereof, or the like. At a terminal part of the track 206, toward a proximal end of the housing 203 (i.e. the end toward the needle and directed toward the patient), the housing 203 includes a first locking member 208 for engagement with a first receiving member (not shown) on, in or through an inner wall of the cradle 205. The first locking member 208 can be a spring-tensioned latch or flange, and the first receiving member can be a hole, aperture, groove, or indentation, receptacle or vice versa. The housing is stationary in this design, attached to the "wings" 212. Shield 202 within the outer housing 203 slide back within the cradle 205 in unison to arm/cock/load the mechanism by stretching the band feature on the elastomeric wings. Once loaded the shield can be deployed by pressing the first receiving member 210 and its associated "button".

The housing 203 further includes an actuator 211, which, like the first locking member 208, can be a spring-tensioned latch or flange, however being biased inward toward the housing as opposed to outward away from the housing like the first locking member 208. The actuator 211 is configured to engage with a corresponding second receiving member (not shown) on, in or through a portion of the cannula hub inside the housing 203. The cradle 205 further includes an elastic member 212, at least a portion of which is in the form of a band or loop that is connected between the cradle 205 and an anchor (not shown) on a distal end of the housing 203 (i.e. an end opposite the needle end and away from the patient), to provide a charged elastomer. The elastic member 212 can also include one or more wings 214 formed of the same material as the charged elastomeric band or loop.

As shown in FIGS. 8A and 9A, when shipped, the needle assembly 200 is in a first state, i.e. a safety mode in which the cradle 205 is latched or otherwise secured toward the distal end of the housing 203, such as by latch 213 shown in FIGS. 8C and 9C, and the cannula hub and needle are likewise retracted toward the distal end of the housing to provide the needle completely within the housing 203 and secure. As shown in FIGS. 8B and 9B, the needle assembly 200 is cocked and ready for use in a second state, i.e. a use mode. In this state, the cradle 205 is slid forward toward the proximal end of the housing 203, to correspondingly move the cannula hub to extend and expose the needle 201 out from the proximal end of the housing. The cradle 205 is slid until it locks in the second state by way of the first locking member 208 engaging with the first receiving member 210. As so slid or moved, the cradle extends and stretches the charged elastomer, which is preferably on an inner surface of the underside of the housing, allowing it to charge its bias toward un-stretching. In some implementations, the elastomer is entirely within the housing, but at least should not protrude below or outside of the housing.

Finally, as shown in FIGS. 8C and 9C, depressing or otherwise actuating the actuator 211 unlocks the charged elastomer which releases the safety shield 202 from a locked state to an unlocked state, and which receives motive energy from the charged elastomer to deploy the safety shield 202 to once again safely secure the needle 201 inside the safety shield 202. As the cradle 205 is locked at the proximal end of the housing 203, and the safety shield 202 is locked in a covered position over the needle, the needle assembly cannot be used again.

FIGS. 10A-10C show a bottom view and FIGS. 11A-11C show a perspective view of the needle assembly 200 shown in FIGS. 8A-8C and 9A-9C, and showing various states or modes of the needle assembly 200. As shown in FIG. 10A, when shipped, the needle assembly 200 is in a first state, i.e. a safety mode, in which the cradle 205 is latched or otherwise secured toward the distal end of the housing 203, and a cannula hub 236 and needle are likewise retracted toward the distal end of the housing to provide the needle completely within the housing 203 where it is secured against accidental or premature needle sticks.

As described above, the needle assembly 200 includes an elastic member 212 connected to a side of the cradle 205, preferably a bottom side of the cradle 205. Opposite the connection to the elastic member 212, the cradle 205 is connected with the cannula hub 236 by a connector via a slot 234 in the housing along a longitudinal axis of the housing. The elastic member 212 can include one or more wings 230, and preferably a pair of wings 230, that extend laterally out from either side of the housing 203. The wings 230 can be folded up to be grasped by a technician for controlling the needle assembly 200, or can remain flat and extended outward so as to be taped to a patient's skin.

The elastic member 212 further includes a band 232 that extends out from the connection point between the elastic member 212 and the cradle 205. In some implementations, the band 232 forms a loop, however in other implementations the band 232 may include a distal end with a loop, connector, shoe fitting, aperture, or other connection mechanism. The band 232 can extend directly out from the connection point, or as shown in FIGS. 11A-11C, can loop around a holding member of the cradle 205 on a first side of the connection point, and then extend beyond the connection point toward the distal end of the housing 203, where it connects to a safety shield connector, i.e. a flange, hook, protrusion, pin, or the like, from the safety shield through a slot in the housing 203 to form a charged elastomer or charged band 232 that is biased to move the safety shield over the needle.

As shown in FIGS. 10B, the needle assembly 200 is cocked and ready for use in a second state, i.e. a use mode. In this state, the cradle 205 is slid forward toward the proximal end of the housing 203, to correspondingly move the housing and safety shield away from the cannula hub 236 to extend and expose the needle 201 out from the proximal end of the housing. The housing is slid relative to the cradle 205 until it locks in the second state by way of the first locking member 208 engaging with the first receiving member 210. As so slid or moved, the cradle extends and stretches the charged elastomer, which is preferably on an underside of the housing, allowing it to charge its bias toward un-stretching. The charged band 232 is thus ready to slide the cannula hub 236 forward toward the proximal end of the housing once a technician releases a locking mechanism that holds the cannula hub 236 in the second state.

Finally, as shown in FIG. 10C, depressing or otherwise actuating the second locking member 210 (as shown in FIG. 8A) unlocks the charged elastomer which deploys or projects the safety shield 202 to at least partially cover the needle 201, which has already been locked into a proximal position within the housing. In some implementations, the safety shield 202 covers at least the tip of the needle with extra clearance, to prevent accidental sticks by the tip of the needle. As the cradle 205 is locked at the proximal end of the housing 203 and the safety shield 202 is locked around the needle 201, the needle assembly cannot be used again. In some implementations, the elastomer is rubber or TPE. In other implementations, a spring can be used, connected between the cradle and the connector of the safety shield, either alone or in conjunction with an elastomeric rubber band.

Figure 12A:
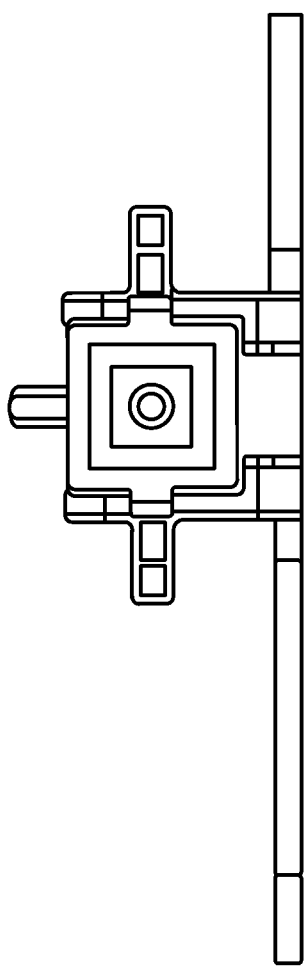
FIGS. 12A, 12B, and 12C show a front view, a perspective view, and a side view, respectively, of the needle assembly in accordance with implementations described herein.
Figure 12C:
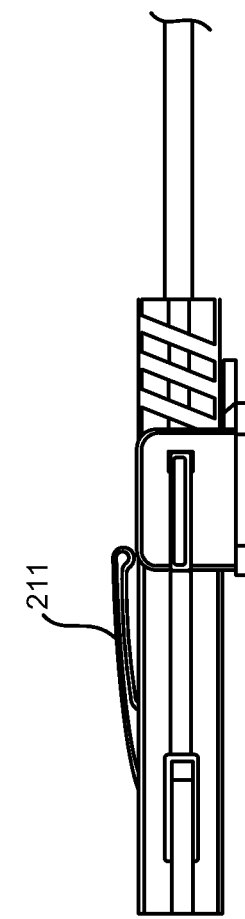
Figure 12B:
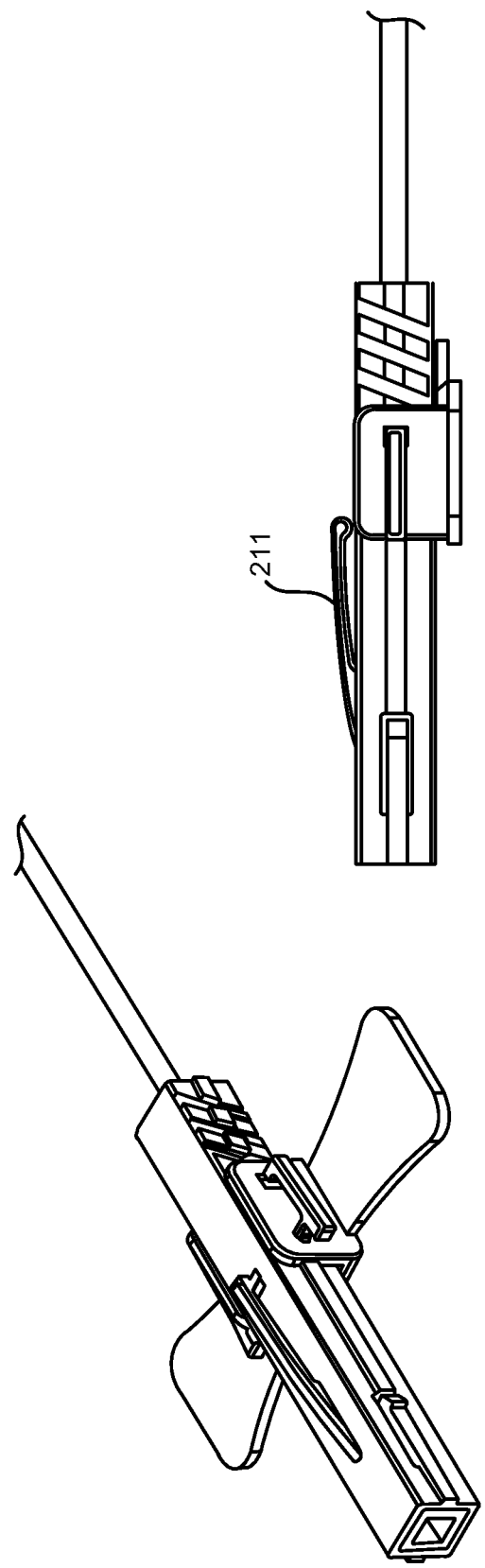

FIGS. 12A, 12B, and 12C show a front view, a perspective view, and a side view, respectively, of the needle assembly 200 in accordance with implementations described herein. In particular, FIG. 12C shows the actuator 211 that, when activated, can cause the safety shield 202 to deploy and cover the needle.

Figure 13A:
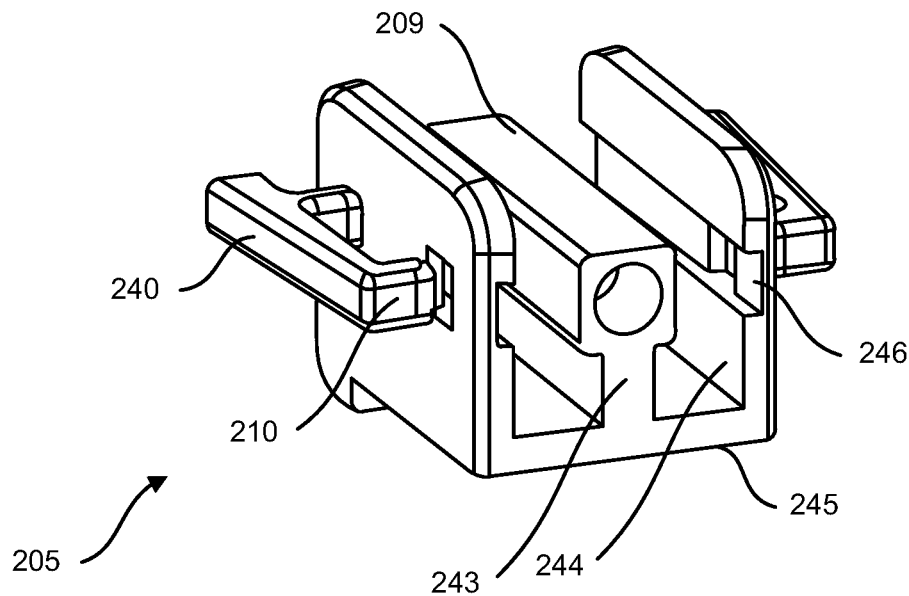
FIGS. 13A and 13B illustrate the cradle, having a cannula hub that forms a tubing bond well and a needle/cannula bond well.
Figure 13B:
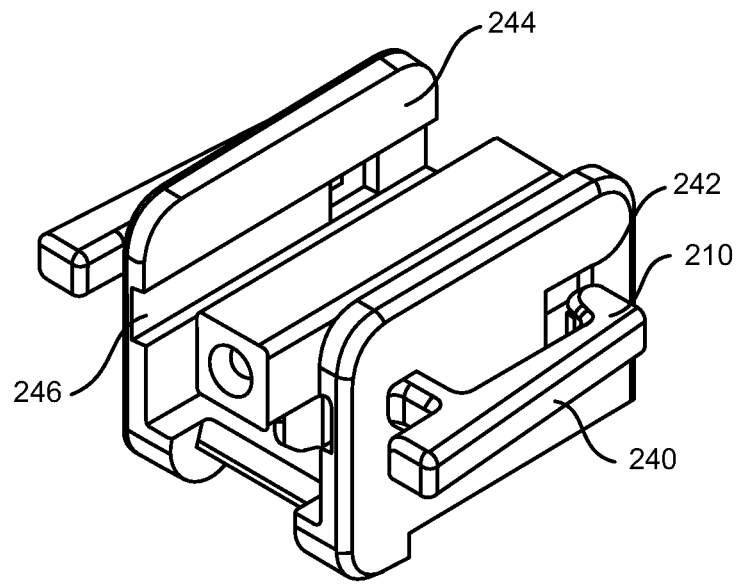

FIGS. 13A and 13B illustrate the cradle 205, having a cannula hub 209 that forms a tubing bond well and a needle/cannula bond well. In some implementations, the cradle 205 includes two side walls 244 connected by a bottom wall 245. The cannula hub 209 extends up from the bottom wall 245 between the two side walls 244. The cradle 205 further includes an activation pawl 240 with second locking member 210, as well as a receiver latch well 242 for receiving the second locking member 210 of the activation pawl 240. One or both inside walls 244 of the cradle 205 can include a groove 246 or track, or other guiding mechanism, that allows the cradle 205 to slide relative to the housing 203 by receiving in the groove 246 a corresponding track (not shown) of the safety shield. The corresponding track can include a receiver latch to mate with the locking member 210.

Figure 14A:
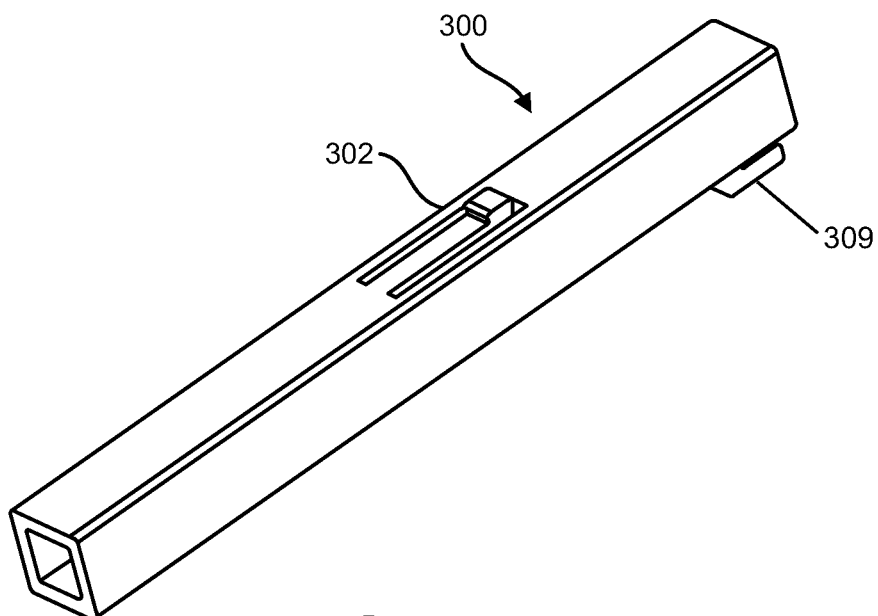
FIG. 14A is a top perspective view and FIG. 14B is a bottom perspective view of the safety shield.
Figure 14B:
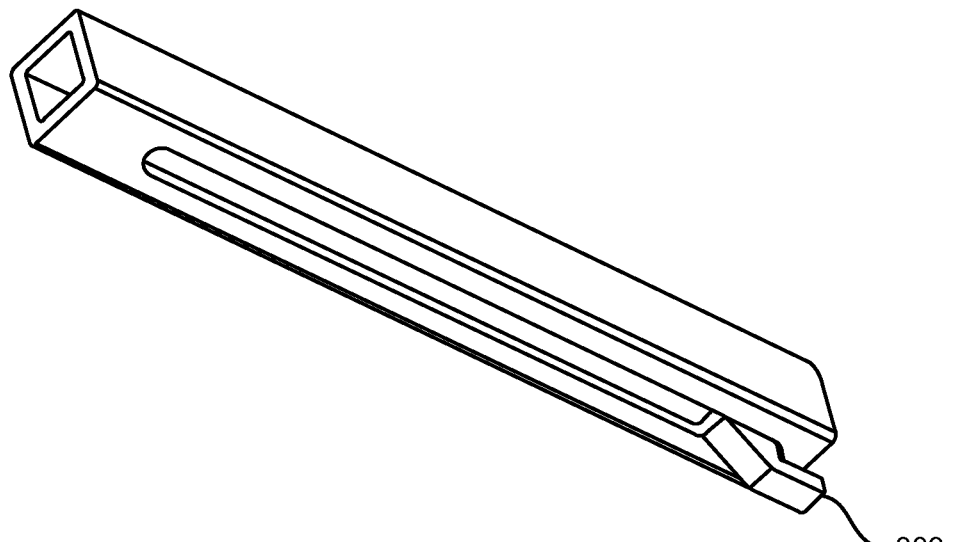

FIG. 14A is a top perspective view and FIG. 14B is a bottom perspective view of the safety shield 300. The safety shield 300 is preferably rectangular with four closed sides and open distal and proximal ends. The safety shield 300 includes an upper receiver latch interface 302, for interfacing with the actuator 211 of the housing 203 that at least partially surrounds the safety shield 300. The safety shield 300 further includes a hook 309, preferably on an opposite side of the upper receiver latch interface 302, for receiving the elastomeric band or spring. The hook 309 can be formed as a curved hook, a latch, a protrusion, a groove, or the like.

Figure 15A:
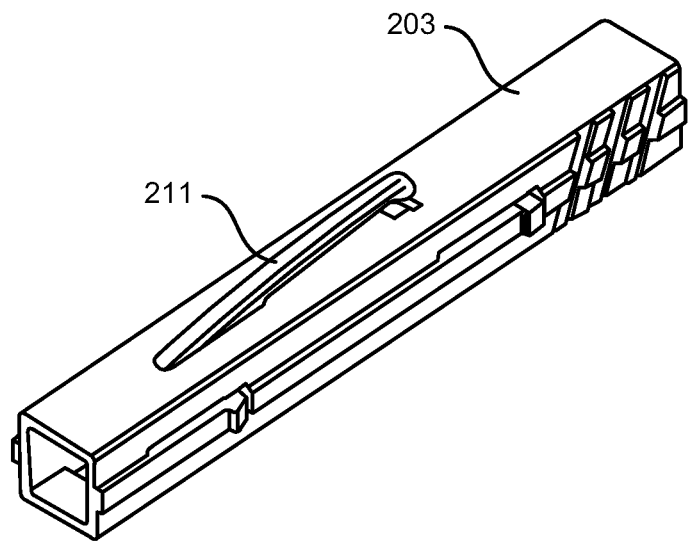
FIG. 15A is a top perspective view and FIG. 15B is a bottom perspective view of the housing.
Figure 15B:
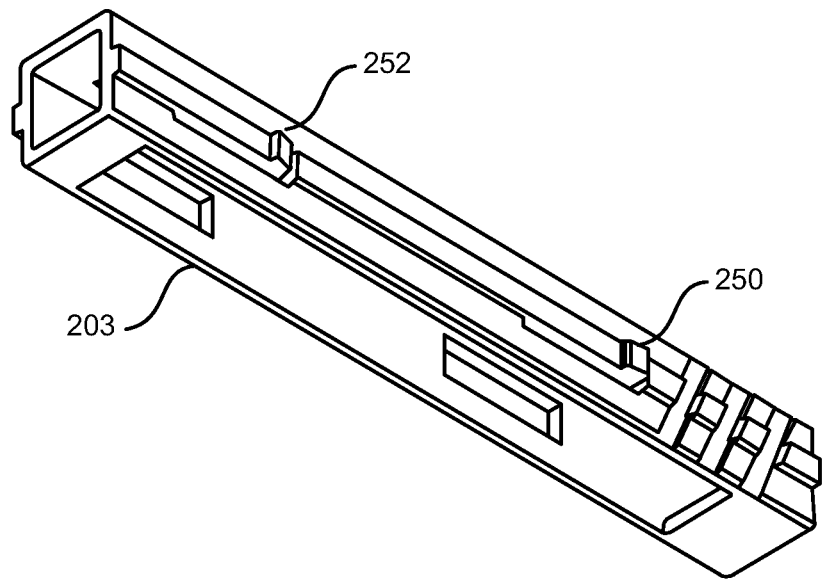

FIG. 15A is a top perspective view and FIG. 15B is a bottom perspective view of the housing 203. The housing 203 includes an actuator 211, which in some implementations include an activation pawl with a latch, and corresponding needle guard latch well. One or more opposing sides of the housing 203 can include cocking release latches 250, as well as a forward travel/charge stop 252.

Figure 16A:
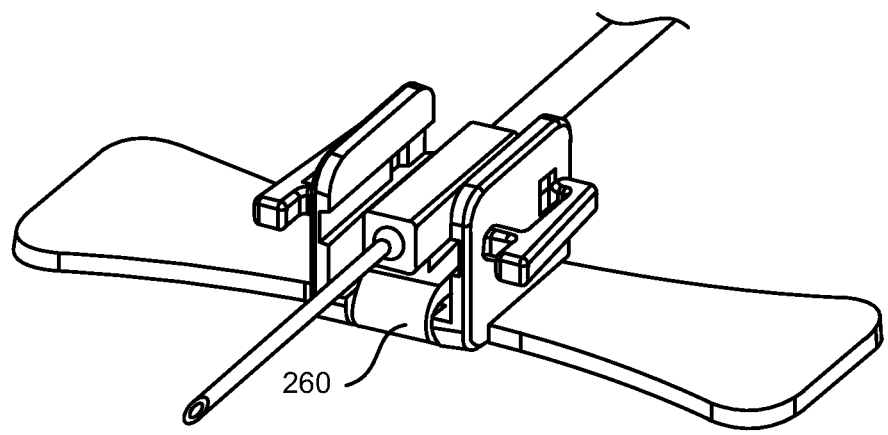
FIGS. 16A and 16B show a proximal perspective view and a distal perspective view of the cradle, respectively, as connected with the tubing and the needle.
Figure 16B:
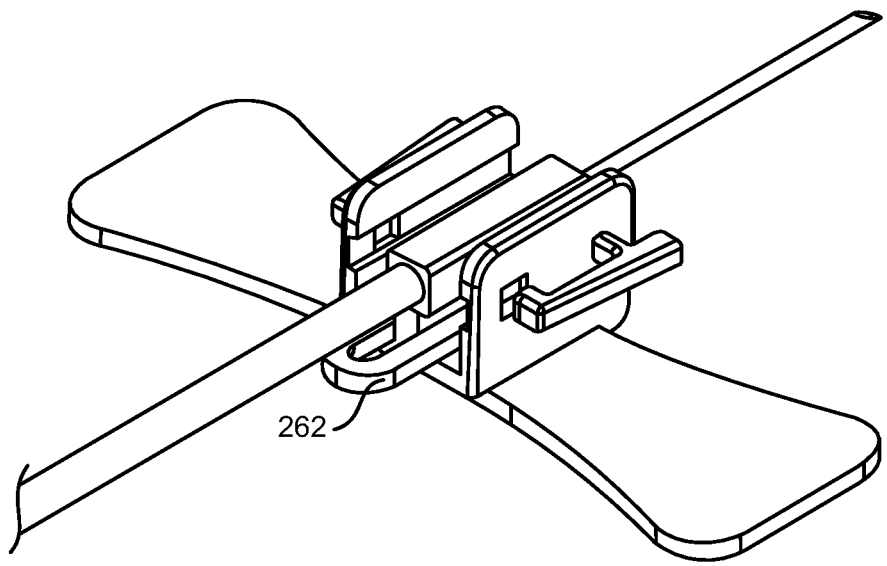

FIGS. 16A and 16B show a proximal perspective view and a distal perspective view of the cradle 203, respectively, as connected with the tubing and the needle. Also shown in FIG. 16A is a tab 260 of the elastic member 212, from which the band 232 extends. The tab 260 is preferably connected under the cannula, and is redirected around an upper surface of a bottom wall of the cradle 203 to a bottom surface of the bottom wall, and extending toward the distal end of the housing. FIG. 16B is a distal perspective view of the cradle 203, showing a second loop 262 of elastic member 212 that connects around extending member 243 (shown in FIG. 13A) that connects to the tubing bond well, and positions the tubing bond well is approximately the center of the cradle 203.

FIGS. 17A and 17B illustrate a needle assembly 300 that connects to tubing 310. The needle assembly 300 includes a housing 302 that at least partially covers a barrel 304, which is retracted into the housing 302 in a first mode to allow a needle 301 to protrude therefrom, as shown in FIG. 17A, and is extended in a second mode to completely cover the needle 301, as shown in FIG. 17B. The barrel 304 defines and forms an encasement with one or more side walls 305 and an end wall 307. The end wall 307 includes one or more apertures through which the needle 301 extends in the first mode. The first mode (FIG. 17A) is how the needle assembly 300 is shipped and prepared for use, and the needle 301 can be initially covered by a removable sheath, such as a plastic tube or the like, which can be discarded after removal.

The housing 302 includes an actuator arm 306, preferably formed as a cut-through between an outer surface and an inner surface of the housing 302, to form an elongated member that can be depressed from the outer surface and allow a distal end of the actuator arm 306 to bend inward. The cut-through can be three-sided to form a rectangular elongated member, or two-sided to form a triangular elongated member. The distal end of the actuator arm 306 can include an actuation region 308. A top side of the actuation region 308 can include a button, a bump, one or more ridges, a raised tab, a depression, or the like, as a target for a user's finger to operate or depress the actuation region 308.

In other implementations, the actuation region 308 is a button configured through the housing 302. The button can be spring loaded toward being raised away from the outer surface of the housing 302. In yet other implementations, the actuation region 308 can simply be a pliably depressable or deformable area or region on the housing 302 that can be depressed from a general plane of the outer surface of the housing 302. A bottom side of the actuation region 308 of the actuator arm 306 interacts with a locking member 311 and locking tab 313 on part of the side wall 305 of the barrel 304 to enable the barrel 304 to transition from the first mode to the second mode, as will be explained in more detail below. One or more guard members 314 can extend from the housing 302 proximate to or around the actuation region 308, to protect against or inhibit unintentional or premature actuation of the actuation region 308 by a user. In some implementations, the guard members 314 can be formed as a raised ridge or wall, and can at least partially or fully surround the actuation region 308.

The housing 302 and the barrel 304 can be made of any combination of a number of synthetic or natural materials, such as polyethylene, polypropylene, polystyrene, polycarbonate, polyether ether ketone (PEEK), or other polyaryletherketone (PAEK) or other plastics, and/or of nylon, carbon fiber, acrylic, or other polymers.

The needle assembly 300 further includes one or more wings 312 that extend laterally from the housing 302. In preferred exemplary implementations, the needle assembly 300 includes a pair of wings 312 extending outwardly from opposing sides of the housing 302 on either side of the actuation region 308. Each wing 312 can be made of a flexible or elastomeric material, such as rubber, so as to be able to be folded up and grasped by a user, for directing and locating the needle 301 for venipuncture, and can include ridges, gripping members or texture on a bottom side that faces downward, so as to be gripped by a user when folded upward. The ridges, gripping members or texture can also assist in adhering the wings to a patient's skin when the wings 312 are positioned downward or extending sideways, the top of the wings 312 preferably being smooth so as to be able to be taped to the patient's skin, if desired.

Figure 19A:
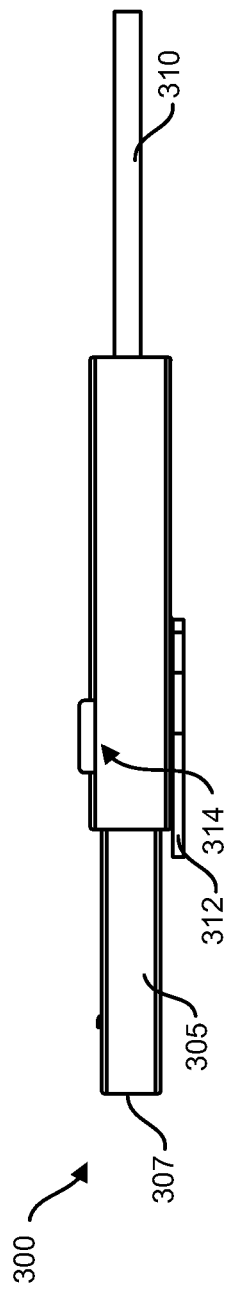
FIGS. 19A-19C are various views of the needle assembly in the second mode in accordance with the implementations described herein.
Figure 19B:
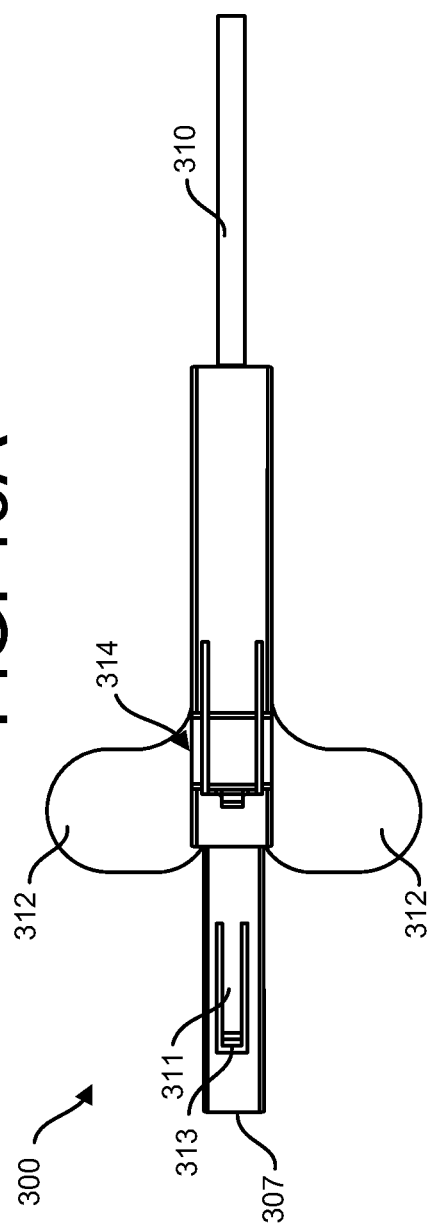
Figure 19C:
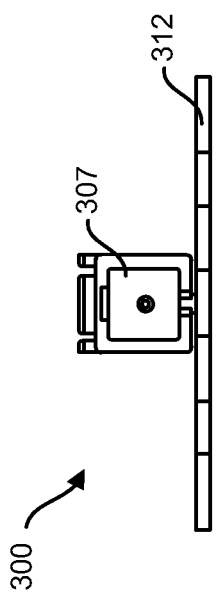

FIG. 18A is a side view, FIG. 18B is top-down view, and FIG. 18C is a front view of the needle assembly 300 that connects to tubing 310 in the first mode in accordance with the implementations described herein. FIG. 19A is a side view, FIG. 19B is a top-down view, and FIG. 19C is a front view of the needle assembly 300 in the second mode in accordance with the implementations described herein.

FIGS. 20A and 20B are cross-sectional, cutaway views of a needle assembly 400 in the first mode and second mode, respectively. As substantially as described above, the needle assembly 400 includes a housing 402 and a barrel 404 that can be deployed as a safety shield around a needle 401. The barrel 404 is retracted at least partially within the housing 402 in the first mode, and extends out from the housing 402 under a biasing force of spring 406 coupled between an inner face 411 or wall of the barrel 404 and a cannula hub 408 that is connected with and maintained in a position with respect to the housing 402.

The barrel 404 can include a forward region 418 that includes parallel walls, having an inner face 411, or inner wall, and an outer face 419, or outer wall, each having an aperture 412 that are substantially aligned with each other in a horizontal axis. Having two or more of the apertures 412 act to stabilize the needle 401, and ensure it is directed in the desired position and/or direction.

The cannula hub 408 holds a portion of a cannula or tubing 410, which can be attached to the cannula hub 408 by glue or other attachment mechanism. In some implementations, the cannula hub 408 includes a channel that is angled downward toward a front of the needle assembly 400, such that a front portion of the cannula or tubing 410 extends from a front side of the cannula hub 408 at a slight angle. The angle can be 0.1 to 10 degrees or more, and preferably 1 to 3 degrees. The needle 401 is attached to the front portion of the cannula or tubing 410 and is biased toward a bottom of the barrel 404, but in the first mode, the needle extends through at least two apertures 412 in the barrel 404 so as to extend from the barrel 404 in an alignment defined by the sequential at least two apertures 412. A first of the at least two apertures 412 can be positioned on a front face of the barrel 404, while a second of the at least two apertures 412 can be positioned within the inner face 411 of the barrel 404. In some implementations, the at least two apertures 412 are aligned substantially at the same height such that the needle 401 extends from the barrel 404 horizontally.

The cannula hub 408 can be attached to, and/or extend up from, one or more wings 414 that extend out laterally from the bottom of the needle assembly 400. Alternatively, the cannula hub 408 can be an extension of, or integrated with, the wall of the housing 402. In some implementations, the one or more wings 414 and cannula hub 408 are formed of a unitary material. The cannula hub 408 extends up through, and can be affixed to, an opening in the housing 402. The cannula hub 408 can also extend through a channel on an underside of the barrel 404, the length of which allows the barrel 404 to extend, slide or move relative to both the housing 402 and the cannula hub 408, as shown in FIG. 20B.

As shown in FIGS. 20A, an actuator arm 420 can be formed as a portion, i.e. a portion of the sidewall, of housing 402, preferably as a cutout in a top surface of the housing 402. The actuator arm 420 can include an actuation region 422 proximal to a distal end of the actuator arm 420. A spring 430 or other biasing mechanism can be coupled between a front region of the barrel and the cannula hub 408, which in turn can be connected with the housing 402. The spring 430 can be initially compressed in the first mode, and biased toward decompression.

The actuator arm 420 of the housing 402 interacts with a locking member 424 portion of the barrel, located underneath the actuator arm 420. The locking member 424 includes a locking flange 426 which in the first mode abuts and locks against latch 428 formed on the housing 402. The latch 428 can have a substantially vertical locking face to abut the locking flange 426, and a sloped face to allow passage of the locking flange 426 once the locking flange 426 is depressed by a user's actuation of the actuation region 422 of the actuator arm 420.

Once the actuation region 422 is actuated, the actuator arm 420 of the housing 402 depresses the locking member of the barrel 404 to disengage the locking flange 426 from the front face of the latch 428, such that the spring 430 decompresses and ejects the barrel 404 forward from its position in the first mode to an extended position in the second mode, as illustrated in FIG. 4B.

In the extended position, or second mode, the barrel 404 and the forward region 418 with apertures 419 extend beyond the needle 401. The cannula hub 408 can be configured to orient the tubing or cannula, as well as the needle 401, at a slight angle, which is preferably downward away from a top of the barrel 404 and/or the housing 402, and which causes the tubing and/or needle 401 to be biased downward as well. This angle will direct the needle 401 down toward a bottom surface of the barrel 404. In this position, the needle 401 cannot protrude from the barrel 404 and it is safely secured. Alternatively, the needle 401 can include a slight curvature or bend, preferably, but not limited to, a downward curvature or bend relative to illustrations in FIGS. 20A and 20B, and the cannula hub 408 may or may not include the angle.

In some implementations, the needle 401 can be biased downward to engage one of an extended number of coils of spring 430 and/or an inner surface of the barrel 404. Further still, an inside face 440 of the distal end of the barrel 404 can inhibit any forward movement of the needle 401, and if formed of a softer material, such as a soft and pliable plastic for example, the inside face 440 can absorb a limited puncture by the needle 401 to lock the needle 401 in a retracted position in the second mode.

FIGS. 21A-21C illustrate a needle assembly 500, and in particular a barrel 504 of a needle assembly. FIG. 21A shows the barrel 504 extended from a housing 502 in a second mode. The barrel 504 includes an enclosure 506 that at least partially encloses a needle in a first mode, and completely encloses the needle in the second mode. The barrel 504 includes a distal end 508 with distal wall 509 and inner wall 511 that is spaced apart from the distal wall 509.

Each of the distal wall 509 and inner wall 511 includes an aperture 510 through which the needle initially extends. The two apertures 510 are positioned and aligned so as to ensure a proper alignment and direction of the needle when extended therethrough. Since the needle is biased downward, in the second mode as the barrel 504 extends to enclose the needle, and the inner wall 511 is extended beyond the distal point of the needle, the needle is directed downward such that access to the needle through either aperture 510 is impossible. A spring 512 coupled between the inner wall 511 and a cannula hub (not shown) within the housing 502 maintains the barrel 504 in the extended, second mode, while the needle itself prevents retraction of the barrel 504 into the housing 502 again.

Figure 22:
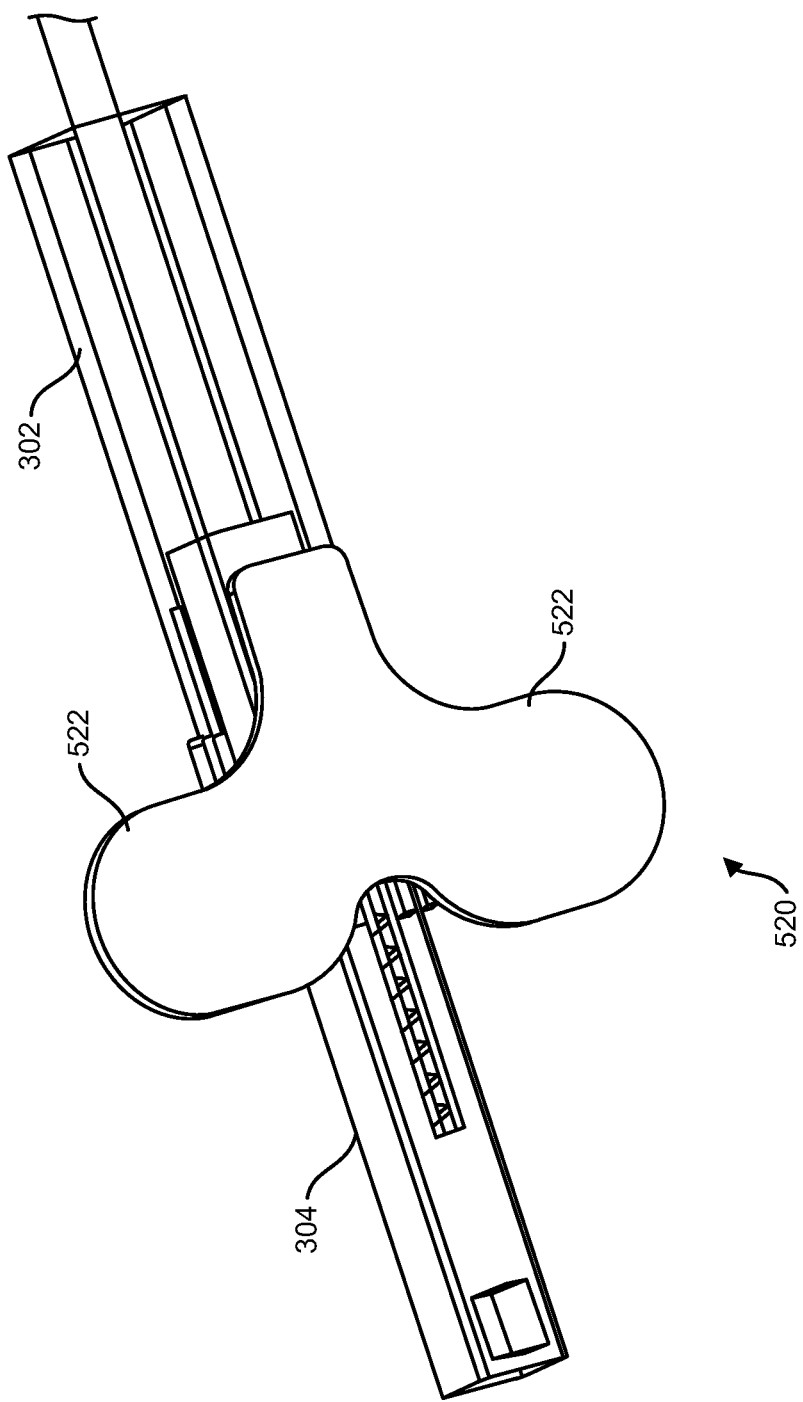
FIG. 22 is a perspective view of an underside of the needle assembly.

FIG. 22 is a perspective view of an underside of the needle assembly 500, with the barrel 504 extended from the housing 502. The needle assembly 500 includes a wing assembly 520 with opposing wings 522 that extend on opposite sides of the housing 502. A bottom surface of the wings 522 can include a texture or pattern of raised portions and/or indentations, so as to allow a user to fold the wings 522 up and grip them while performing a venipuncture when the needle assembly is in the first mode (i.e. needle extended).

Although a few embodiments have been described in detail above, other modifications are possible. Other embodiments may be within the scope of the following claims.

The invention claimed is:

1. A safety needle assembly for venipuncture of a patient, the safety needle assembly comprising:
    a housing a needle;
    a barrel adapted to be secured in a first mode to be substantially locked within the housing and extended from the housing in a second mode;
    a cradle connected with the needle, the cradle being movable from a first position in which the needle is retracted in the housing, to a second position in which the needle is extended from the housing and the cradle is locked in the second position; and
    an elastic member configured to be charged by moving the cradle from the first position to the second position, and configured to propel the barrel to the second mode to cover the needle upon actuation of a release mechanism,
    the safety needle assembly being further configured such that movement of the cradle from the first position to the second position stretches the elastic member and thereby charges the elastic member.

2. The safety needle assembly in accordance with claim 1, further comprising an actuator configured to actuate the transitioning of the barrel from the first mode to the second mode.

3. The safety needle assembly in accordance with claim 1, further comprising a pair of wings extending sideward on opposite sides of the housing.

4. The safety needle assembly in accordance with claim 3, wherein the pair of wings are foldable to at least connect at their respective distal ends to enable a user to grasp the pair of wings.

5. The safety needle assembly in accordance with claim 1, the cradle further comprising a cannula hub, wherein the cradle is connected to the needle via the cannula hub.

6. The safety needle assembly in accordance with claim 1, wherein the elastic member is an elastomeric band coupled between the barrel and the cradle.

7. The safety needle assembly in accordance with claim 1, wherein the elastic member does not protrude outside of the housing.

8. The safety needle assembly in accordance with claim 7, wherein the elastic member is entirely within the housing.

9. The safety needle assembly in accordance with claim 1, the housing comprising a first locking member configured to engage a first receiving member to lock the cradle in the second position.

* * * * *